United States Patent
Kojima et al.

(10) Patent No.: US 11,268,900 B2
(45) Date of Patent: *Mar. 8, 2022

(54) POLARIZATION PROPERTY IMAGE MEASUREMENT DEVICE, AND POLARIZATION PROPERTY IMAGE MEASUREMENT METHOD

(71) Applicant: NIKON CORPORATION, Tokyo (JP)

(72) Inventors: Takanori Kojima, Kuroishi (JP); Satoru Odate, Tokyo (JP); Toru Takagi, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,474

(22) Filed: Feb. 4, 2020

(65) Prior Publication Data
US 2020/0173911 A1    Jun. 4, 2020

Related U.S. Application Data

(63) Continuation of application No. 16/003,882, filed on Jun. 8, 2018, now Pat. No. 10,620,116, which is a (Continued)

(30) Foreign Application Priority Data

Dec. 11, 2015 (JP) .............................. JP2015-242559

(51) Int. Cl.
*G01N 21/21* (2006.01)
*G01N 21/31* (2006.01)
(Continued)

(52) U.S. Cl.
CPC ......... *G01N 21/21* (2013.01); *A61B 1/00009* (2013.01); *A61B 1/04* (2013.01); (Continued)

(58) Field of Classification Search
CPC .... G01N 21/21; G01N 21/251; G01N 21/314; G01N 2021/216; G01N 2021/4792; (Continued)

(56) References Cited

U.S. PATENT DOCUMENTS

2005/0041249 A1* 2/2005 Dobbs ................... G01N 21/21
356/364
2008/0049224 A1 2/2008 Otsuki et al.
(Continued)

FOREIGN PATENT DOCUMENTS

JP 2003-270095 9/2003
JP 2007-139751 6/2007
(Continued)

OTHER PUBLICATIONS

Japanese Office Action dated Jan. 12, 2021 in Japanese Patent Application No. 2020-024300.
(Continued)

*Primary Examiner* — Jamil Ahmed

(57) ABSTRACT

A polarization property image measurement device includes: a first radiation unit that radiates light beams in different polarization conditions onto a target object after subjecting the light beams to intensity modulation at frequencies different from one another; a light receiving unit including first photoelectric conversion units that photoelectrically convert the light beams having been radiated from the first radiation unit and scattered at the target object in correspondence to each of the different polarization conditions, and second photoelectric conversion units that photoelectrically convert visible light from the target object; and a processor that detects signals individually output from the first photoelectric conversion units at the different frequencies and differentiates each signal from other signals so as to determine an origin of the signal as one of the light beams; and creates an image of the target object based upon signals individually output from the second photoelectric conversion units.

19 Claims, 26 Drawing Sheets

Related U.S. Application Data continuation of application No. PCT/JP2016/086877, filed on Dec. 12, 2016.

(51) Int. Cl.

| | | |
|---|---|---|
| G01N 21/25 | (2006.01) | |
| G01J 3/51 | (2006.01) | |
| G01J 3/28 | (2006.01) | |
| G01J 3/02 | (2006.01) | |
| G01J 4/04 | (2006.01) | |
| G01J 4/00 | (2006.01) | |
| G01J 3/00 | (2006.01) | |
| H01L 27/146 | (2006.01) | |
| G06T 15/00 | (2011.01) | |
| A61B 1/06 | (2006.01) | |
| A61B 1/00 | (2006.01) | |
| A61B 1/04 | (2006.01) | |
| G06T 7/521 | (2017.01) | |
| G01N 21/47 | (2006.01) | |
| G01J 1/42 | (2006.01) | |

(52) U.S. Cl.
CPC ............ *A61B 1/0646* (2013.01); *G01J 3/00* (2013.01); *G01J 3/0224* (2013.01); *G01J 3/28* (2013.01); *G01J 3/2803* (2013.01); *G01J 3/513* (2013.01); *G01J 4/00* (2013.01); *G01J 4/04* (2013.01); *G01N 21/251* (2013.01); *G01N 21/314* (2013.01); *G06T 7/521* (2017.01); *G06T 15/005* (2013.01); *H01L 27/1462* (2013.01); *H01L 27/14621* (2013.01); *H01L 27/14627* (2013.01); *H01L 27/14645* (2013.01); *H01L 27/14649* (2013.01); *G01J 2001/4242* (2013.01); *G01J 2003/2806* (2013.01); *G01J 2003/516* (2013.01); *G01N 2021/216* (2013.01); *G01N 2021/4792* (2013.01); *G01N 2201/067* (2013.01); *H01L 27/14636* (2013.01)

(58) Field of Classification Search
CPC . G01N 2201/067; G06T 7/521; G06T 15/005; A61B 1/00009; A61B 1/04; A61B 1/0646; G01J 3/00; G01J 3/0224; G01J 3/28; G01J 3/2803; G01J 3/513; G01J 4/00; G01J 4/04; G01J 2001/4242; G01J 2003/2806; G01J 2003/516; H01L 27/1462; H01L 27/14621; H01L 27/14627; H01L 27/14645; H01L 27/14649; H01L 27/14636
See application file for complete search history.

(56) References Cited

U.S. PATENT DOCUMENTS

| | | | |
|---|---|---|---|
| 2009/0051916 A1* | 2/2009 | Otani | G01N 21/21 356/364 |
| 2014/0368618 A1 | 12/2014 | Ushinaga et al. | |
| 2015/0035980 A1 | 2/2015 | Krökel | |
| 2015/0077590 A1 | 3/2015 | Kuriyama et al. | |
| 2015/0206912 A1 | 7/2015 | Kanamori et al. | |
| 2015/0256733 A1* | 9/2015 | Kanamori | G02F 1/0136 348/234 |

FOREIGN PATENT DOCUMENTS

| | | |
|---|---|---|
| JP | 2012-10757 | 1/2012 |
| JP | 2012-10763 | 1/2012 |
| JP | 2012-24140 | 2/2012 |
| JP | 2012-24142 | 2/2012 |
| JP | 2012-24146 | 2/2012 |
| JP | 2012-24252 | 2/2012 |
| JP | 2012-24283 | 2/2012 |
| JP | 2012-40224 | 3/2012 |
| JP | 2012-45029 | 3/2012 |
| JP | 2014-108193 | 6/2014 |
| JP | 2015-33587 | 2/2015 |
| JP | 2015-065524 | 4/2015 |
| JP | 2015-180864 | 10/2015 |
| WO | WO 2013/094121 | 6/2013 |
| WO | WO 2013/164915 | 11/2013 |
| WO | WO-2013164915 A1 * | 11/2013 ........... H04N 5/3454 |
| WO | WO 2015/015722 | 2/2015 |

OTHER PUBLICATIONS

International Search Report dated Apr. 25, 2017 in corresponding International Patent Application No. PCT/JP2016/086877.
English Translation by the International Searching Authority of the Written Opinion for International Patent Application No. PCT/JP2016/086877, dated Apr. 25, 2017, 12 pgs.
Japanese Office Action dated Jun. 11, 2019 in corresponding Japanese Patent Application No. 2017-555180.
Japanese Office Action dated Dec. 17, 2019 in Japanese Patent Application No. 2017-555180.
U.S. Office Action dated Oct. 3, 2019 in U.S. Appl. No. 16/003,882.
U.S. Notice of Allowance dated Dec. 18, 2019 in U.S. Appl. No. 16/003,882.
U.S. Appl. No. 16/003,882, filed Jun. 8, 2018, Takanori Kojima, et al., Nikon Corporation.
Abiri, B. et al., "A 1-D Heterodyne Lens-Free Optical Phase Array Camera With Reference Phase Shifting," IEEE Photonics Journal, vol. 10, Issue 5, pp. 1-12 (Abstract only).
Notice of Reasons for Rejection, dated Aug. 17, 2021, in Japanese Patent Application No. 2020-024300 (9 pp.).

\* cited by examiner

POLARIZATION PROPERTY IMAGE MEASUREMENT DEVICE, AND POLARIZATION PROPERTY IMAGE MEASUREMENT METHOD

This application is a continuation of U.S. patent application Ser. No. 16/003,882 filed Jun. 8, 2018, which is a continuation of International Application No. PCT/JP2016/086877 filed Dec. 12, 2016.

INCORPORATION BY REFERENCE

The disclosures of the following priority applications are herein incorporated by reference:
Japanese Patent Application No. 2015-242559 filed Dec. 11, 2015
International Application No. PCT/JP2016/086877 filed Dec. 12, 2016
U.S. application Ser. No. 16/003,882 filed Jun. 8, 2018

BACKGROUND ART

1. Technical Field

The present invention relates to a polarization property image measurement device and a polarization property image measurement method.

2. Description of Related Art

There is a method practised in the related art whereby the characteristics of a target object are examined by irradiating the target object with light, capturing an image formed with reflected light and analysing the captured image. Japanese Laid Open Patent Publication No. 2015-33587 discloses a polarization image measurement/display system that executes polarization conversion processing on a plurality of sets of light intensity image information, generated in correspondence to a plurality of polarized light beams in different polarization conditions which are reflected at a test subject so as to convert the plurality of sets of light intensity image information to a plurality of sets of polarization property image information indicating different polarization properties.

SUMMARY

The polarization image measurement/display system disclosed in the above publication sequentially radiates a plurality of polarized light beams in different polarization conditions in order to obtain a single polarization property image, and thus, sets of data corresponding to the plurality of polarized light beams radiated to generate a single polarization property image are obtained at different time points. There is an added issue in that the data acquisitions at different time points are bound to impose limitations with regard to frame rate or exposure time.

A polarization property image measurement device according to a first aspect of the present invention comprises: a first radiation unit that radiates a plurality of light beams in different polarization conditions onto a target object after subjecting the plurality of light beams to intensity modulation at frequencies different from one another; a light receiving unit including a plurality of first photoelectric conversion units that photoelectrically convert the light beams having been radiated from the first radiation unit and scattered at the target object in correspondence to each of the different polarization conditions, and a plurality of second photoelectric conversion units that photoelectrically convert visible light from the target object; and a processor that is configured to: detect signals individually output from the plurality of first photoelectric conversion units at the different frequencies and differentiates each signal from other signals so as to determine an origin of the signal as one of the plurality of light beams; and create an image of the target object based upon signals individually output from the plurality of second photoelectric conversion units.

A polarization property image measurement method according to a second aspect of the present invention, comprises: radiating a plurality of light beams in different polarization conditions from a first radiation unit onto a target object after subjecting the plurality of light beams to intensity modulation at different frequencies; photoelectrically converting light beams having been radiated from the first radiation unit onto the target object and scattered at the target object with a plurality of first photoelectric conversion units, in correspondence to each of the different polarization conditions; photoelectrically converting visible light from the target object with a plurality of second photoelectric conversion units; detecting signals individually output from the plurality of first photoelectric conversion units at the different frequencies so as to differentiate each signal from others, so as to determine an origin of the signal as a light beam having a polarization condition among the light beams in the different polarization conditions.

A polarization property image measurement device according to a third aspect of the present invention comprises: a first radiation unit that radiates a plurality of light beams in different polarization conditions onto a target object after subjecting the plurality of light beams to intensity modulation executed at different phases; a light receiving unit including a plurality of first photoelectric conversion units that photoelectrically convert the light beams having been radiated from the first radiation unit and scattered at the target object in correspondence to each of the different polarization conditions; and a processor that is configured to detect signals individually output from the plurality of first photoelectric conversion units at the different phases and differentiates each signal from other signals so as to determine an origin of the signal as one of the plurality of light beams.

DESCRIPTION OF EMBODIMENTS

Figure 1:
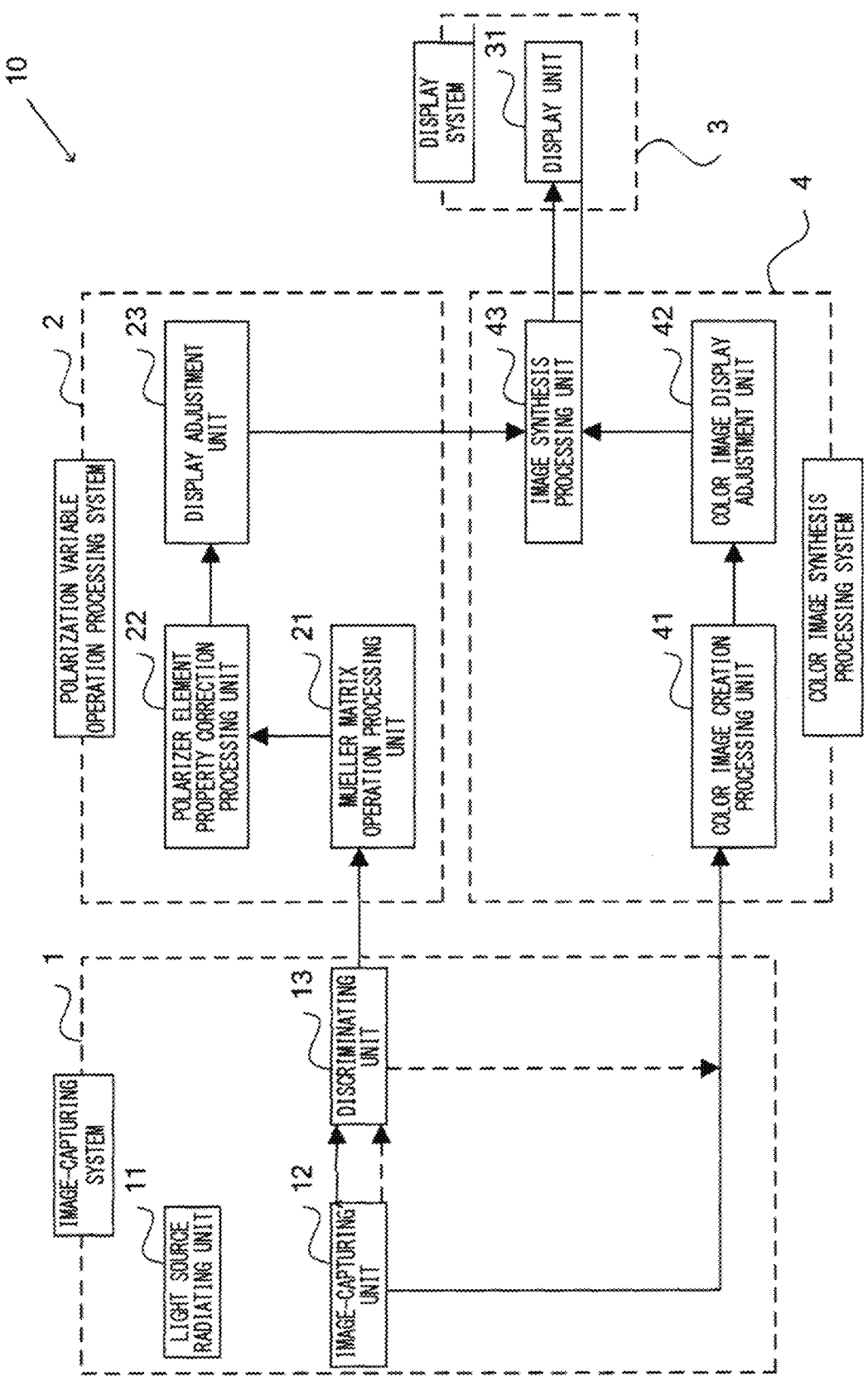
FIG. 1 is a schematic block diagram pertaining to a polarization property image measurement device achieved in a first embodiment.

FIG. 1 is a diagram showing functional blocks in a polarization property image measurement device 10 achieved in a first embodiment. The polarization property image measurement device 10 comprises an image-capturing system 1, a polarization variable operation processing system 2, a display system 3 and a color image synthesis processing system 4. The image-capturing system 1 includes a light source radiating unit 11, an image-capturing unit 12 and a discriminating unit 13. The polarization variable operation processing system 2 includes a Mueller matrix operation processing unit 21, a polarizer element property correction processing unit 22 and a display adjustment unit 23. The display system 3 includes a display unit 31. The color image synthesis processing system 4 includes a color image creation processing unit 41, a color image display adjustment unit 42 and an image synthesis processing unit 43. The arrows in the diagram indicate how image information pertaining to a captured image flows.

The image-capturing system 1 is configured as a Mueller matrix image-capturing system capable of measuring a Mueller matrix indicating the polarization characteristics of a target object. The light source radiating unit 11, the image-capturing unit 12 and the discriminating unit 13 do not need to be disposed in physical proximity to one another and they may be disposed at positions a significant distance from one another by using a communication line such as an optical fiber. While some of the functions of the discriminating unit 13 may be fulfilled in the operation processing system, an image sensor 100 in the embodiment is capable of fulfilling the function of the discriminating unit 13 in an optimal manner and for this reason, the discriminating unit 13 is included in the image-capturing system 1.

The light source radiating unit 11 radiates a plurality of light beams having polarization conditions different from one another by modulating their intensities at frequencies different from one another. The term "polarization condition" in this context refers to a condition pertaining to the angle (direction) of linearly polarized light or a condition pertaining to the direction along which circularly polarized light rotates. The light source radiating unit 11 is capable of controlling a plurality of light beams having polarization conditions different from one another, independently of one another and radiating the light beams at desired time points. This means that the light source radiating unit 11 is able to simultaneously radiate the individual light beams having different polarization conditions. The light source radiating unit 11 may adopt a structure that allows it to individually radiate the plurality of light beams having different polarization conditions via a plurality of radiation ports, or the plurality of light beams may be radiated through a single radiation port through multiplexing. The light source radiating unit 11 will be described in detail later.

The image sensor 100 is disposed in the image-capturing unit 12. The image sensor 100 photoelectrically converts a plurality of light beams, radiated to the target object from the light source radiating unit 11 and scattered at the target object, individually in correspondence to polarization conditions different from one another. The scattered light includes the light radiated toward the target object and scattered at the target object either to be reflected off the target object or pass through the target object. The image sensor 100 includes a plurality of polarization detection pixels that receive light beams having the various polarization conditions. At a given polarization detection pixel, light radiated from the light source radiating unit 11, which assumes a predefined polarization condition, undergoes photoelectric conversion. In other words, light beams in different polarization conditions each undergo photoelectric conversion at one of the different polarization detection pixels in the image sensor 100. A pixel signal obtained via each polarization detection pixel is provided to the discriminating unit 13.

The image sensor 100 further includes a plurality of color pixels at which visible light having departed the target object undergoes photoelectric conversion. The color pixels, via which the color, the shape and the like of the target object are detected, are used to create an image representing the external appearance of the target object. The color pixels are also used to create an image of an external appearance of the target object characterized through calculation executed based upon the pixel values indicated at the color pixels as needed. Based upon pixel signals output from the color pixels, a color image of the target object is generated.

It is to be noted that the image sensor may adopt a structure that enables generation of a display image that includes a specific organic structure at the surface of, or inside the target object through arithmetic operation processing executed as needed based upon the pixel signals output from the color pixels. The optimal light that may be radiated in such an application will be light in a narrow wavelength range that demonstrates pronounced absorption or scattering characteristics at the target organic structure. More specifically, the use of blue-color light and green-color light with the wavelength range narrowed so as to ensure that the radiated light is well absorbed by hemoglobin, will be optimal in creating a display image of a capillary vessel or a deep blood vessel. In addition, the image sensor may adopt a structure that includes color pixels (which may be single-color pixels) capable of photoelectric conversion of electromagnetic waves instead of visible light, for purposes of target object shape detection. An image of the target object generated via such color pixels may be a monochrome image or a pseudo-color image. The image sensor 100 will be described in further detail later.

The pixel signals output from the color pixels are provided to the color image creation processing unit 41 in the color image synthesis processing system 4.

It is to be noted that the pixel signals from the color pixels may be differentiated through intensity modulation and demodulation executed in combination, in much the same way as in the polarization condition detection. In such a case, the pixel signals output from the color pixels may be first transmitted from the image-capturing unit 12 to the discriminating unit 13 and the pixel signals having undergone differentiation processing at the discriminating unit 13 may then be provided to the color image creation processing unit 41 (see the dotted-line arrows in FIG. 1)

The discriminating unit 13 detects or extracts a signal at a frequency having been used for the intensity modulation at the light source radiating unit 11 among outputs from each polarization detection pixel in the image sensor 100, identifies it as a light signal having one of a plurality of polarization conditions different from one another and outputs the light signal thus differentiated. At the light source radiating unit 11, the light beams in the various polarization conditions undergo intensity modulation at different frequencies. Accordingly, the discriminating unit 13 is able to identify the component of the signal output from the polarization detection pixel in the image sensor 100 as a component having originated from a light beam having a specific polarization condition having been radiated from the light source radiating unit 11, by detecting the output signals at frequencies having been used for the intensity modulation. The discriminating unit 13 concurrently detects the signals output from the individual polarization detection pixels in the image sensor 100. In the following description, the component in a pixel signal identified based upon a specific combination of a polarization condition on the radiation side and a polarization condition on the detection side, will be referred to as a polarization property signal. The discriminating unit 13 outputs the individual polarization property signals to the Mueller matrix operation processing unit 21. The specific method of differentiation adopted in the discriminating unit 13 will be described in detail later.

The polarization variable operation processing system 2 calculates Mueller matrices by using the polarization property signals output from the image-capturing system 1 and creates a polarization property image based upon the Mueller matrices thus calculated.

The Mueller matrix operation processing unit 21 restores the amplitude of a light beam in a polarization condition corresponding to the polarization property signal output from each pixel and input thereto, which represents a polarization condition, and calculates various elements in a 4×4 Mueller matrix. The Mueller matrix operation processing unit 21 in the embodiment calculates a Mueller matrix for each pixel unit block 81 (see FIGS. 7A and 7B) that includes pixels, each of which selectively receives a light beam in one of four different polarization conditions, i.e., 0°, 45°, 90° and rightward-rotating circular polarization (hereafter referred to as rightward circular polarization).

However, the types of, and the number of different polarization conditions are not limited to those described above, as long as a desired Mueller matrix can be calculated. In addition, the image sensor 100 may be configured with types of polarization detection pixels different from those described above and the number of polarization detection pixel types is also not limited to that described above. Mueller matrix data calculated in correspondence to each pixel unit block 81 are provided to the polarizer element property correction processing unit 22.

The Mueller matrix can be calculated based upon the amplitudes of the polarization property signals by adopting a method of the known art, as is briefly described below.

A Mueller matrix M indicating the polarization characteristics of the target object is expressed as a 4×4 matrix having a component mij over i rows and j columns, as in (1) below.

$$M = (mij)(i,j=1,2,3,4) \quad (1)$$

Light beams in the various polarization conditions, i.e., 0°, 45°, 90° and rightward circular polarization, radiated from the light source radiating unit 11 correspond to Stokes vectors 51 through S4 (the following mathematical formulae will include arrows representing vectors) in (2) below.

$$\vec{S}_1 = \begin{bmatrix} 1 \\ 1 \\ 0 \\ 0 \end{bmatrix}, \vec{S}_2 = \begin{bmatrix} 1 \\ -1 \\ 0 \\ 0 \end{bmatrix}, \vec{S}_3 = \begin{bmatrix} 1 \\ 0 \\ 1 \\ 0 \end{bmatrix}, \vec{S}_4 = \begin{bmatrix} 1 \\ 0 \\ 0 \\ 1 \end{bmatrix} \quad (2)$$

The light beams in the various polarization conditions represented by the Stokes vectors above are scattered at the target object and are converted to Stokes vectors MS1 through MS4 below, which are each calculated as the product of initial Stokes vector and the target object Mueller matrix, as expressed in (3) below.

$$M\vec{S}_1 = \begin{bmatrix} m_{11} \\ m_{21} \\ m_{31} \\ m_{41} \end{bmatrix} + \begin{bmatrix} m_{12} \\ m_{22} \\ m_{32} \\ m_{42} \end{bmatrix}, M\vec{S}_2 = \begin{bmatrix} m_{11} \\ m_{21} \\ m_{31} \\ m_{41} \end{bmatrix} - \begin{bmatrix} m_{12} \\ m_{22} \\ m_{32} \\ m_{42} \end{bmatrix},$$

$$M\vec{S}_3 = \begin{bmatrix} m_{11} \\ m_{21} \\ m_{31} \\ m_{41} \end{bmatrix} + \begin{bmatrix} m_{13} \\ m_{23} \\ m_{33} \\ m_{43} \end{bmatrix}, M\vec{S}_4 = \begin{bmatrix} m_{11} \\ m_{21} \\ m_{31} \\ m_{41} \end{bmatrix} + \begin{bmatrix} m_{14} \\ m_{24} \\ m_{34} \\ m_{44} \end{bmatrix} \quad (3)$$

A Stokes vector S is generally calculated as expressed in (4) below through polarization measurement. l0, l45, l90, l135, lR and lL are values equivalent to light intensities corresponding to 0°, 45°, 90°, 135°, rightward circular polarization and leftward rotating circular polarization (hereafter referred to as leftward circular polarization), which can be calculated based upon the amplitudes of the light beams in the various polarization conditions. The values l0, l45, l90, l135, lR and lL are not entirely independent of one another, and some of them can be determined through cross calculation.

$$\vec{S} = \begin{pmatrix} I_0 + I_{90} \\ I_0 - I_{90} \\ I_{45} - I_{135} \\ I_R - I_L \end{pmatrix} = \begin{pmatrix} I_0 + I_{90} \\ I_0 - I_{90} \\ 2I_{45} - I_0 - I_{90} \\ 2I_R - I_0 - I_{90} \end{pmatrix} \quad (4)$$

Accordingly, once the Stokes vectors MS1 through MS4 are determined by calculating the amplitudes based upon the polarization property signals corresponding to the light beams in the various polarization conditions, obtained via the discriminating unit 13, the various components mij in the 4×4 Mueller matrix can be calculated as expressed in (5) below $$\begin{bmatrix} m_{11} \\ m_{21} \\ m_{31} \\ m_{41} \end{bmatrix} = \frac{1}{2}(\vec{MS_1} + \vec{MS_2}), \quad (5)$$

$$\begin{bmatrix} m_{12} \\ m_{22} \\ m_{32} \\ m_{42} \end{bmatrix} = \frac{1}{2}(\vec{MS_1} + \vec{MS_2}),$$

$$\begin{bmatrix} m_{13} \\ m_{23} \\ m_{33} \\ m_{43} \end{bmatrix} = \vec{MS_3} - \frac{1}{2}(\vec{MS_1} + \vec{MS_2}),$$

$$\begin{bmatrix} m_{14} \\ m_{24} \\ m_{34} \\ m_{44} \end{bmatrix} = \vec{MS_4} - \frac{1}{2}(\vec{MS_1} + \vec{MS_2})$$

The polarizer element property correction processing unit 22 corrects variance in the values indicated in the calculation results for the Mueller matrix obtained at the Mueller matrix operation processing unit 21, the cause of which is attributable to factors inherent to the particular polarization property image measurement device, such as misalignment in the polarization patterning between the light source and the pixels. The polarizer element property correction processing will be described in detail later. The Mueller matrix data, having been corrected, are then provided to the display adjustment unit 23.

The display adjustment unit 23 analyses and processes the Mueller matrix data having been calculated in correspondence to each of the pixel unit blocks so as to create and adjust a polarization property image in conformance with a display mode. The polarization property image is a display image that provides polarization property information obtained through imaging. The display adjustment unit 23 extracts an optimal parameter for the examination of the physical properties of the target object from the Mueller matrix and generates a polarization property image by two-dimensionally mapping the parameter. No particular limitations are imposed with regard to the parameter extracted for purposes of examining the physical properties of the target object. However, it is desirable to extract a parameter that cannot be recognized in the visible image and makes it possible to distinguish the target object from the surrounding environment as the parameter to be used to examine the physical properties of the target object. The part of the target object that assumes characteristics defined by such a parameter can be identified via the polarization property image measurement device 10.

For instance, it is known in the application field of diagnostic imaging equipment, such as endoscopes, that biological tissue can be distinguished through polarization analysis executed based upon uniformity of the biological tissue, anisotropy of the biological tissue, the orientation of fibers and the like. If there is randomly-growing tumor tissue amidst tissue with cells set with a certain order, e.g., fiber orientation, the location of a lesion can be identified through polarization measurement by examining the degree of depolarization, in which the anisotropy of the tissue or the like is reflected.

It is desirable that the display adjustment unit 23 be able to map data over the imaging range by extracting a diagonal component in a Mueller matrix and, more specifically, the M22 component or the M33 component in the 4×4 Mueller matrix, as the parameter. The M22 component or the M33 component in the 4×4 Mueller matrix is known to be useful for identification of cancerous tissue in diagnostic imaging.

The display adjustment unit 23 may create the polarization property image as a skeleton image that shows the identified area by enhancing the boundary between the area and the surrounding area. In addition, the display adjustment unit 23 may color the identified area by using a pseudo-color. Through these means, the visibility of the identified area in a synthesized image created by combining the polarization property image and the color image, is improved. The polarization property image thus created is provided to the image synthesis processing unit 43.

The display system 3 is configured with the display unit 31 at which a synthesized image created by combining the polarization property image and the color image of the target object is brought up on display for the user. No particular limitations are imposed with regard to the display unit 31, as long as an image created in the embodiment can be brought up on display thereat. The display unit 31 may be constituted with any image display device such as a liquid crystal monitor.

The color image synthesis processing system 4 creates a color image and creates a synthetic image by combining the color image with the polarization property image output from the polarization variable operation processing system 2. The color image creation processing unit 41 creates a color image based upon color pixel signals, i.e., red (R) pixel signals, green (G) pixel signals and blue (B) pixel signals output from the image-capturing system 1. The color image thus generated is adjusted by the color image display adjustment unit 42 so as to optimize it for the synthesis processing through which it is combined with the polarization property image. The color image, having been adjusted, is provided to the image synthesis processing unit 43.

The image synthesis processing unit 43 creates a synthetic image by combining the polarization property image provided from the display adjustment unit 23 and the color image provided from the color image display adjustment unit 42. The synthetic image thus created is provided to the display unit 31.

The discriminating unit 13, the polarization variable operation processing system 2 and the color image synthesis processing system 4, or parts of these functional blocks may be configured as physical blocks in the form of processing circuits laminated at the image sensor 100.

Figure 2:
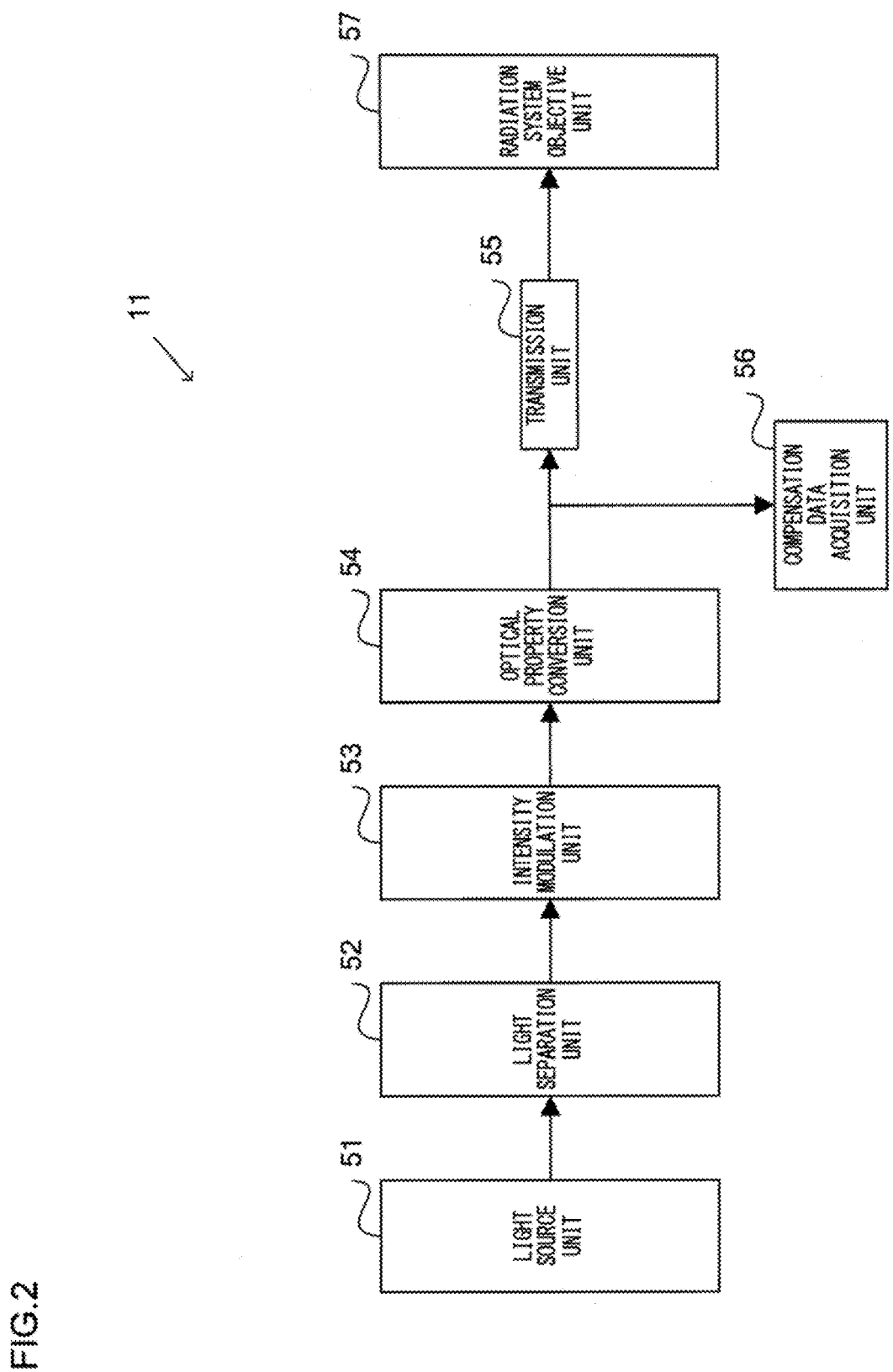
FIG. 2 is a schematic block diagram pertaining to a light source radiating unit in the first embodiment.

FIG. 2 is a diagram showing the functional blocks in the light source radiating unit 11. The light source radiating unit 11 includes a light source unit 51, a light separation unit 52, an intensity modulation unit 53, an optical property conversion unit 54, a transmission unit 55, a compensation data acquisition unit 56 and a radiation system objective unit 57. The arrows in the figure indicate the advancing path through which light emitted from the light source unit 51 advances.

The light source unit 51 includes a light source that emits light, used as a radiation light source. No particular limitation is imposed with regard to the light source, as long as light from the light source can be radiated toward the target object, as in the embodiment. The light source unit 51 may be configured with a white light lamp such as a fluorescent lamp, a mercury lamp, a white light LED, a laser that emits laser light in a specific narrow wavelength range, a monochrome LED or the like. Polarization measurement can be executed by using monochromatic light, light within a specific wavelength range and white light in a wide wavelength range that contains the wavelengths of visible light and near-infrared light. The wavelength range of light emitted from the light source unit 51 contains part of, or all of a range covering the visible range, which may be defined as a 400 nm through 700 nm range, through the near-infrared range, which may be defined as a 700 nm through 2500 nm range. It is desirable that the light source unit 51 emit visible light. The light source unit 51 in the embodiment emits white light. The light emitted from the light source unit 51 enters the light separation unit 52.

It is to be noted that while the term "white light" used in the description of the embodiment refers to light that contains red-color light, green-color light and blue-color light which can be detected at the individual color pixels as described later, it does not impose any limitation with regard to the particulars of the invention and that it may be any light containing light in various wavelength ranges. For instance, white light may contain light assuming successive intensities each corresponding to a specific wavelength within the visible range, or light assuming successive intensities each corresponding to a specific wavelength in the non-visible range, such as the near-infrared range.

The light separation unit 52 splits the light emitted from the light source unit 51 into separate light beams via an optical element such as a beam splitter. The individual light beams separated from one another via the light separation unit 52 enter the intensity modulation unit 53.

It is to be noted that while the white light emitted from the light source unit 51 is split into separate beams at the light separation unit 52 in the example described above, a plurality of light beams may be generated by using different light sources instead, as long as the data indicating the amplitudes and the like of the individual light beams can be quantitatively compared.

The intensity modulation unit 53, constituted with an electro-optic modulator (EOM), an acousto-optic modulator (AOM) or the like, modulates the intensity of the individual light beams at frequencies different from one another. When light beams in polarization conditions corresponding to various frequencies are simultaneously radiated, scattered light beams having undergone polarization conversion at the target object become superimposed one upon another in pixel signals resulting from photoelectric conversion. As a result, a frequency assuming a value representing the sum of frequency values among the frequency values having been set or a value representing the difference between two such frequency values will manifest at a multiplier circuit during a detection phase, as will be described later. Accordingly, in order to extract the target polarization condition through detection with accuracy, it should be ensured that the sum of, or the difference between a given pair of frequencies does not take a value equal to the value of any of the frequencies having been used for the intensity modulation or the value of a frequency used in another detection method. The individual light beams having undergone the intensity modulation at the intensity modulation unit 53 enter the optical property conversion unit 54.

The optical property conversion unit 54, constituted with an optical element, converts the optical properties of light having entered therein. Namely, the plurality of light beams having entered the optical property conversion unit 54 are each converted to a light beam assuming a polarization conditions different from others via a polarizer, a phase shifter, or the like. A polarizer that may be used for this polarization condition conversion may be a polarizing plate, whereas a phase shifter that may be used for the polarization condition conversion may be a phase-difference plate and more specifically a λ/4 wave plate. In addition, the optical property conversion unit 54 also converts the light to be used for color image creation to light in a narrower wavelength range, and more specifically to monochromatic light, via a wavelength filter or the like.

The light source radiating unit 11 in the embodiment radiates light beams in four different polarization conditions, i.e., 0°, 45°, 90° and rightward circular polarization, in order to enable measurement of 4×4 Mueller matrix. The optical property conversion unit 54 generates light beams in the 0° polarization condition, the 45° polarization condition and the 90° polarization condition by allowing the individual light beams, having entered therein after departing the intensity modulation unit 53, to be polarized through polarizing plates assuming the corresponding polarization directions. The optical property conversion unit 54 generates rightward circularly polarized light by allowing a light beam, having entered therein after departing the intensity modulation unit 53, to pass through a 45° polarizing plate and a λ/4 wave plate.

It is to be noted that the optical property conversion unit 54 may generate leftward circularly polarized light or light in a 135° polarization condition, instead of the rightward circularly polarized light. By using light assuming the 135° polarization condition, the third component S3 (refer to the expression (2)) in the Stokes vector can be measured with high accuracy (refer to the expression (4)). Light in this polarization condition is particularly useful when 3×3 Mueller matrix needs to be measured with high accuracy by using light beams in four different polarization conditions without having to measure circularly polarized light.

Once the predetermined types of radiation light beams are generated at the optical property conversion unit 54, each light beam is split into two separate beams at an optical element such as a beam splitter and the separate light beams enter the transmission unit 55 and the compensation data acquisition unit 56.

The transmission unit 55 is configured with a transmission path such as an optical fiber through which light is transmitted. By adjusting the length of the transmission unit 55, the distance between the area where the light source unit 51, the light separation unit 52, the intensity modulation unit 53 and the optical property conversion unit 54, engaged in radiation light adjustment, are disposed and the radiation system objective unit 57, which will be described later, can be altered. Light, having passed through the transmission unit 55, enters the radiation system objective unit 57.

It is to be noted that a transmission unit 55 may be disposed as needed between various functional blocks in the light source radiating unit 11.

The compensation data acquisition unit 56 obtains data to be used as compensation data for the polarizer element by sampling the radiated light. In addition, it generates a reference signal that will be needed for detection at the discriminating unit 13, from the radiated light, and outputs the reference signal thus generated to the discriminating unit 13. The compensation data acquisition unit 56, which may be configured with a compact image sensor such as a line sensor, includes an optical filter corresponding to a polarization condition resulting from the conversion at the optical property conversion unit 56, disposed at each pixel thereof. The compensation data acquisition unit 56 samples the frequencies used to modulate the intensity of the light beams assuming the various polarization conditions by individually detecting light beams assuming polarization conditions different from one another. In addition, the compensation data acquisition unit 56 detects the variance in the light intensity in correspondence to each optical property, generates compensation data to be used to correct the intensity variance and outputs the compensation data thus generated to the polarizer element property correction processing unit 22, which will be described in detail later.

It is to be noted that the compensation data acquisition unit 56 and the optical element such as a beam splitter, via which light is split and directed toward the compensation data acquisition unit 56, may be disposed further toward the radiation system objective unit 57 relative to the transmission unit 55. Such a configuration will make it possible to shorten the communication distance over which the compensation data and the reference signal need to be transmitted and ultimately to provide the device as a compact unit, particularly if the discriminating unit 13 is disposed in closer proximity to the radiation system objective unit 57 rather than the light source unit 51. In addition, the reference signal may be output from the intensity modulation unit 53 instead of the compensation data acquisition unit 56. In such a case, a signal indicating a frequency having been used for modulation at the intensity modulation unit 53 will be output as a reference signal.

The radiation system objective unit 57 outputs the radiation light having passed through the transmission unit 55 toward the target object. The radiation system objective unit 57, constituted with, for instance, a diffusion lens, is adjusted as needed in correspondence to the characteristics of the target object.

It is to be noted that while the light having departed the light separation unit 52 first undergoes intensity modulation and then undergoes optical property conversion in the example described above, the light having departed the light separation unit 52 may instead first undergo optical property conversion such as polarization condition conversion and then undergo intensity modulation.

<Description of Laminated Image Sensor>

Figure 3:
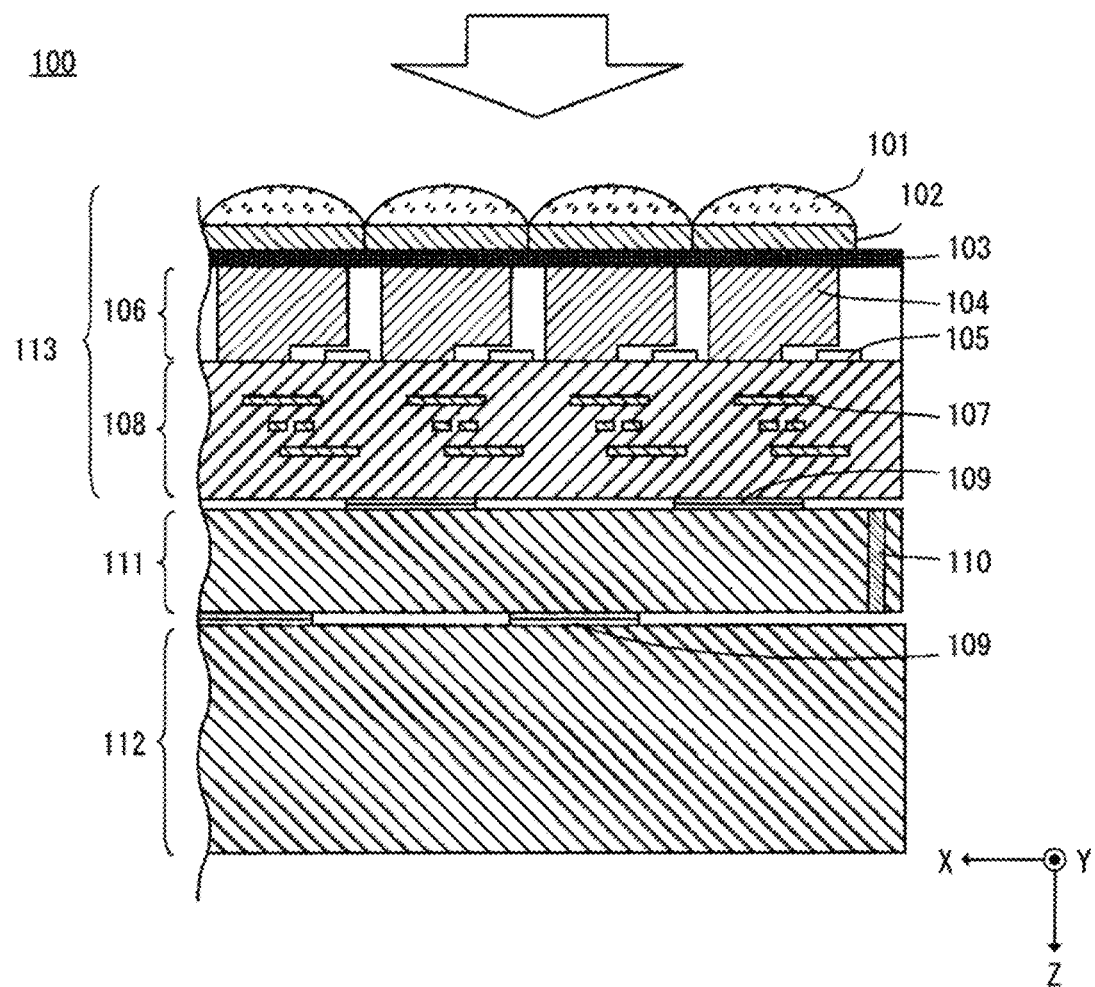
FIG. 3 is a sectional view of a laminated image sensor.

The laminated or stacked image sensor 100 included in the image-capturing unit 12 will be described next. It is to be noted that the laminated image sensor 100 is identical to that disclosed in the WO 13/164915 publication pertaining to an application previously submitted by the applicant of the present invention. FIG. 3 is a sectional view of the laminated image sensor 100. The image sensor 100 comprises a back-side illuminated image-capturing chip 113 that outputs pixel signals corresponding to incident light, a signal processing chip 111 that processes the pixel signals and a memory chip 112 where the pixel signals are stored. The image-capturing chip 113, the signal processing chip 111 and the memory chip 112 are laminated one upon another and are electrically connected with one another via bumps 109 constituted of a material having electrical conductivity such as Cu.

As illustrated in the figure, incident light advances mainly along the direction indicated with the unfilled arrow. In the description of the embodiment, the surface of the image-capturing chip 113, located on the side where the incident light enters, will be referred to as the back side (image-capturing surface).

The image-capturing chip 113 may be, for instance, a back side illuminated MOS image sensor. A PD layer 106 is disposed at the back side of a wiring layer 108. In the PD layer 106, a plurality of PDs (photodiodes) 104 laid out in a two-dimensional pattern in which electric charges corresponding to the incident light are accumulated, and transistors 105, each disposed in correspondence to one of the PDs, are present.

A filter layer 102 is disposed via a passivation film 103 on the entry side of the PD layer 106 where the incident light enters. Polarization filters or color filters can be disposed as needed in the filter layer 102. A polarization filter, constituted with a polarizer element such as a polarization patterning element and/or a phase shifter such as a phase difference plate and more specifically a λ/4 wave plate, extracts a polarization condition such as 0°, 45°, 90° or 135° relative to a predetermined reference direction or polarization conditions such as rightward circular polarization, leftward circular polarization or the like. A plurality of types of color filters that allow light in wavelength ranges different from one another to be transmitted can be used.

Microlenses 101 are disposed each in correspondence to one of the pixels on the entry side of the filter layer 102 where the incident light enters the filter layer 102. A microlens 101 condenses the incident light toward the corresponding PD 104.

Wirings 107, through which pixel signals from the PD layer 106 are transmitted to the signal processing chip 111, are present in the wiring layer 108. The wirings 107 may assume a multilayer structure and may include a passive element and an active element disposed therein.

A plurality of bumps 109 are disposed at the surface of the wiring layer 108. As the plurality of bumps 109 are aligned with a plurality of bumps 109 disposed at the surface of the signal processing chip 111 facing opposite the wiring layer surface and the image-capturing chip 113 and the signal processing chip 111 are, for instance, pressed against each other, the bumps 109 aligned relative to each other become bonded, thereby achieving electric connection.

Likewise, a plurality of bumps 109 are disposed at the surfaces of the signal processing chip 111 and the memory chip 112 facing opposite each other. As these bumps 109 are aligned relative to each other and the signal processing chip 111 and the memory chip 112 are, for instance, pressed against each other, the bumps 109 aligned relative to each other become bonded, thereby achieving electric connection.

It is to be noted that the bumps 109 may be bonded together through micro bump bonding achieved by way of solder fusion, instead of the Cu bump bonding achieved by way of solid phase diffusion. In addition, it suffices to dispose a bump 109 in correspondence to, for instance, a single block, e.g., a pixel unit block to be described later. This means that the size of the bumps 109 may be greater than the pitch at which the PDs 104 are disposed. In addition, bumps larger the bumps 109 corresponding to the pixel area may be disposed in the peripheral area outside the pixel area where the pixels are arrayed.

The signal processing chip 111 includes a TSV (through silicone via) 110 that connects circuits, disposed at the front surface and the back surface of the signal processing chip 111, with each other. It is desirable that the TSV 110 be disposed in a peripheral area. In addition, TSVs 110 may be also disposed in a peripheral area of the image-capturing chip 113 and at the memory chip 112.

The image sensor 100 structured as described above includes a processing circuit that enables high-speed sampling at 10 kHz and higher and processes a signal to be output from each of the pixels disposed at the image sensor 100. It is physically configured as the principal element fulfilling some of, or all of the functions of the discriminating unit 13 in the functional block diagram presented in FIG. 1.

Figure 4:
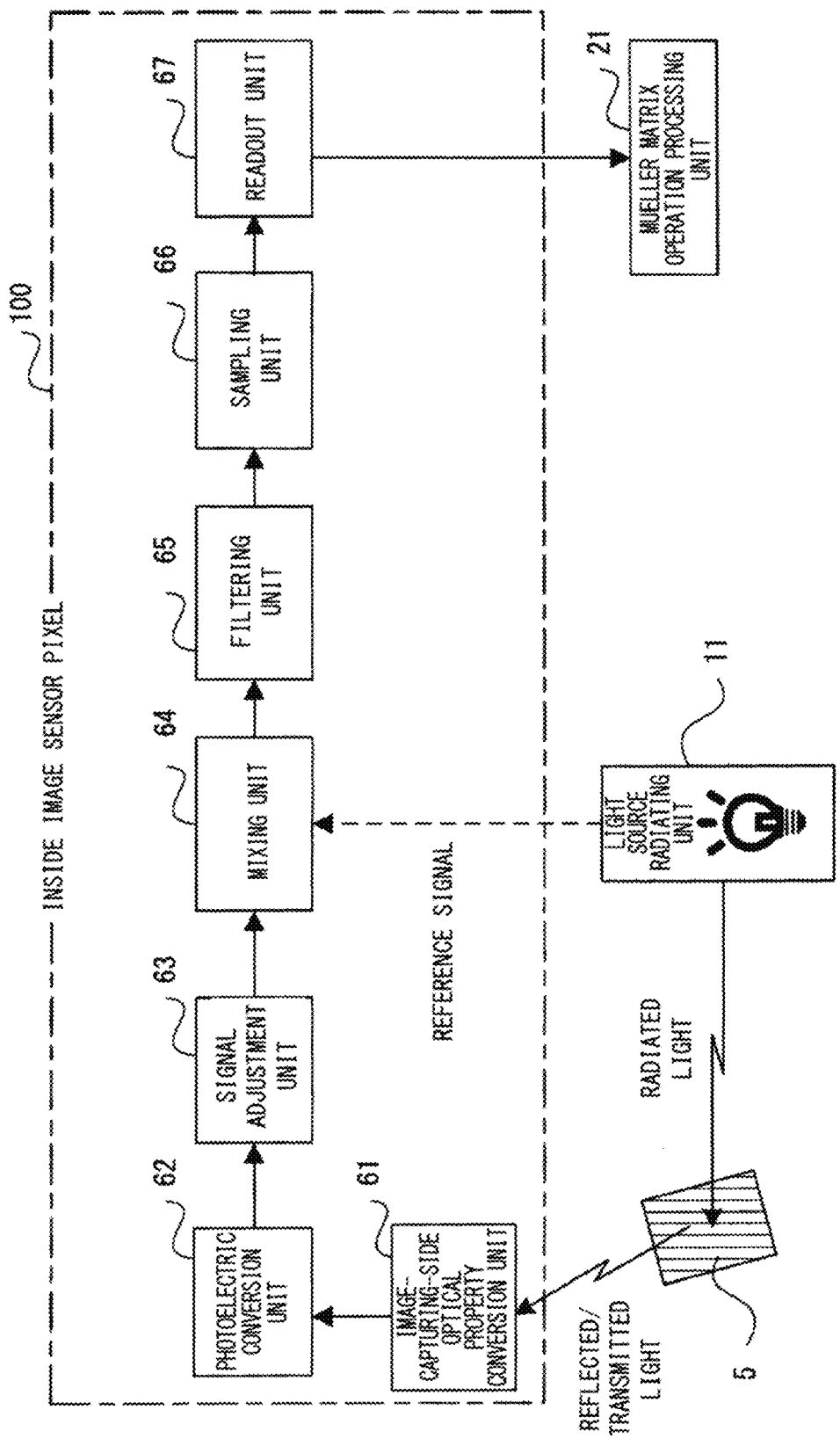
FIG. 4 is a diagram illustrating how waves are detected at the laminated image sensor.

FIG. 4 is a schematic diagram showing the functional blocks pertaining to the image sensor 100 engaged in detection executed within the image sensor 100. The image sensor 100 includes an image-capturing-side optical property conversion unit 61, a photoelectric conversion unit 62, a signal adjustment unit 63, a mixing unit 64, a filtering unit 65, a sampling unit 66 and a readout unit 67. The arrows in the diagram indicate the flow of light, signals and information.

Within the pixels at the image sensor 100, detection processing is executed in correspondence to each pixel so as to extract a component, corresponding to the frequency having been used for the intensity modulation, from the pixel signal generated with the light having entered the particular pixel.

The light radiated from the light source radiating unit 11 is first scattered at a target object 5 before entering the image-capturing-side optical property conversion unit 61. The image-capturing-side optical property conversion unit 61, constituted with a polarization filter and/or a phase difference plate or the like, such as those described earlier, is utilized so as to ensure that a light beam in a specific polarization condition enters each pixel. It is to be noted that the image-capturing-side optical property conversion unit 61 may be constituted with a color filter or the like instead of a polarization filter in order to detect a color image signal. The light having passed through the image-capturing-side optical property conversion unit 61 enters the photoelectric conversion unit 62.

The photoelectric conversion unit 62, which converts incident light to a pixel signal such as an electric current, is constituted with a PD, an avalanche PD, a phototransistor or the like. The pixel signal output from the photoelectric conversion unit 62 is input to the signal adjustment unit 63.

The signal adjustment unit 63 adjusts the pixel signal in preparation for frequency separation through, for instance, current/voltage conversion. The signal adjustment unit 63 includes a current-voltage conversion circuit equivalent to, for instance, a trans-impedance amplifier. In addition, depending upon the detection method adopted, the output signal may be divided into separate signal portions, which then individually undergo phase conversion, or the like as needed and are output to a plurality of mixing units 64.

The mixing unit 64 generates a signal with a frequency different from the frequency of the input signal based upon a reference signal provided from the light source radiating unit 11. The mixing unit 64 includes a multiplier circuit and a phase conversion circuit. The reference signal is output from the compensation data acquisition unit 56 shown in FIG. 2. While no particular limitations are imposed with regard to the reference signal as long as it contains a frequency component required for the detection, it may include, for instance, a sine wave, a cosine wave or a rectangular wave in a frequency having been used for the intensity modulation.

Assuming that a given component in the radiation light has undergone intensity modulation at a frequency F1 in homodyne detection, the pixel signal having undergone the photoelectric conversion at the photoelectric conversion unit 62 will contain F1 or a frequency (F1+ΔF1) close to F1. Accordingly, a lock-in method, for instance, may be adopted so as to extract the signal component resulting from the intensity modulation as a low-frequency component (F1+ΔF1)−F1=ΔF1 equivalent to the difference between the frequency of the pixel signal and the frequency of the reference signal by calculating the product of the pixel signal and the reference signal at the frequency F1 in the multiplier circuit of the mixing unit 64. The mixing unit 64 outputs a light beam containing a specific frequency component, such as the low-frequency component obtained as described above, to the frequency filtering unit 65.

It is to be noted that while the homodyne detection method is adopted in the example described above, no particular limitations are imposed with regard to the detection method, as long as a component corresponding to the frequency having undergone the intensity modulation can be extracted.

At the filtering unit 65, the specific frequency component, having been obtained at the mixing unit 64, is extracted through filter processing. The filtering unit 65 is constituted with a filtering circuit equivalent to a bandpass filter, a low-pass filter or the like. The pixel signal, having undergone the filter processing at the filtering unit 65, is output to the sampling unit 66.

The sampling unit 66 samples the pixel signal at a specific frequency so as to prepare for pixel signal analog/digital conversion (hereafter referred to as A/D conversion). The sampling unit 66 includes a sampling circuit and a holding circuit. The pixel signal output from the sampling unit 66 is input to the readout unit 67.

The pixel signal input to the readout unit 67 undergoes A/D conversion. The readout unit 67 includes an A/D conversion circuit. The pixel signal having undergone the A/D conversion at the readout unit 67 is input to the Mueller matrix operation processing unit 21 (see FIG. 1).

It is desirable that readout processing be executed in the readout units 67 within the individual polarization detection pixels in synchronization with one another. It is even more desirable that the readout processing in the readout units 67 be executed in synchronization for all the pixel signals used to generate a single polarization property image. Through such measures, a polarization property image demonstrating a high level of simultaneity, with only a slight time lag, shorter than the signal readout cycles of the image sensor 100, can be obtained.

It is to be noted that while the detection is executed in the image sensor 100 in the example described above, detection may instead be executed via a device having an equivalent detection capability such as a duel-phase lock-in amplifier, disposed outside the image sensor 100. In addition, the digital signal resulting from the A/D conversion may undergo frequency separation through, for instance, a Fourier transform.

It is to be noted that the processing executed in the filtering unit 65 and beyond in FIG. 4 may be instead executed outside the image sensor 100. In such a case, a more efficient device configuration with, for instance, a shorter reference signal transmission distance, may be achieved particularly if the light source radiating unit 11 and the image sensor 100 are disposed in close proximity to each other.

Figure 5:
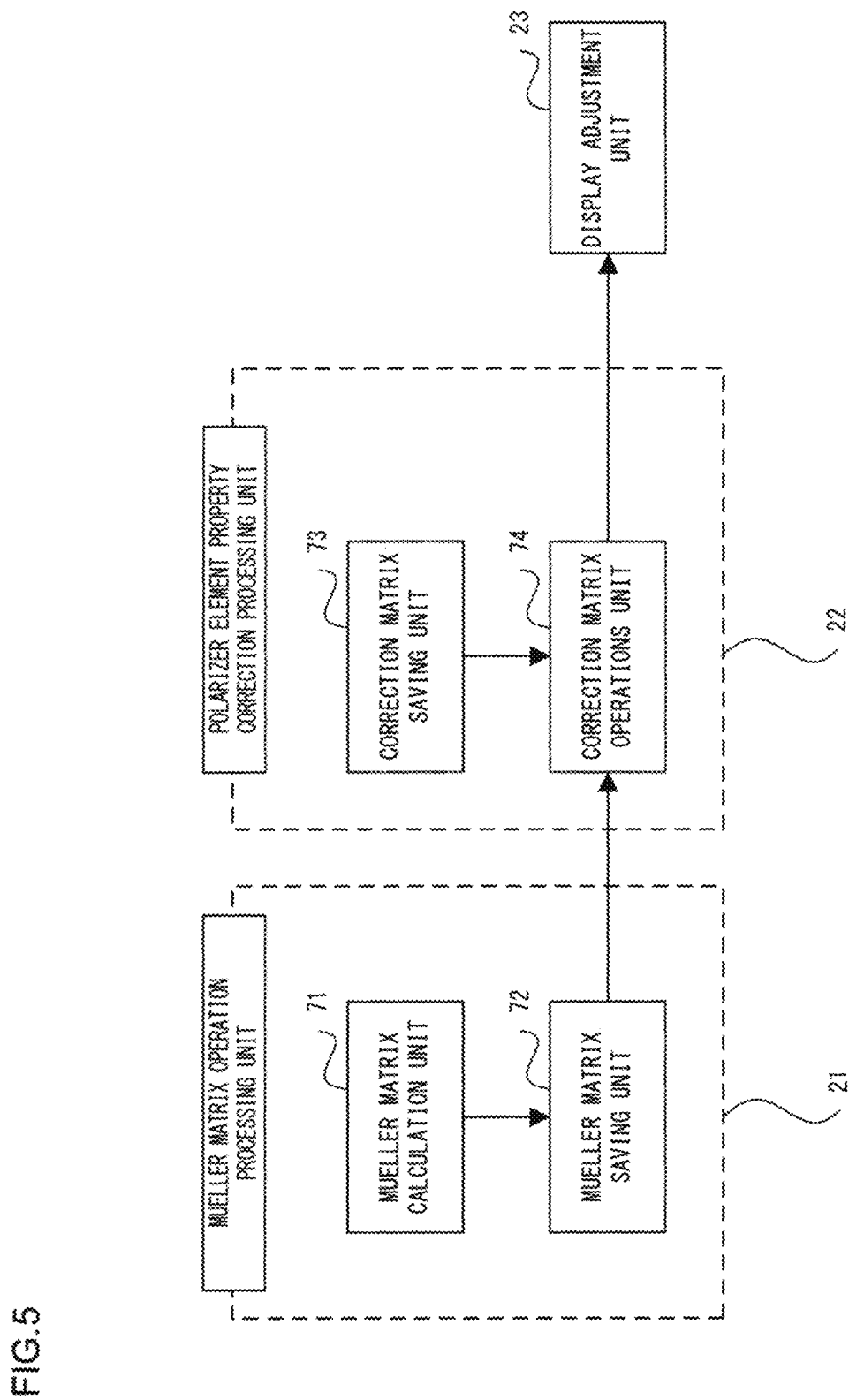
FIG. 5 is a schematic block diagram pertaining to a polarization variable operation processing system achieved in an embodiment.

FIG. 5 is a block diagram showing the flow of polarizer element property correction processing. The Mueller matrix operation processing unit 21 includes a Mueller matrix calculation unit 71 and a Mueller matrix saving unit 72. The polarizer element property correction processing unit 22 includes a correction matrix saving unit 73 and a correction matrix operation unit 74. The arrows in the figure indicate how information flows.

The Mueller matrix calculation unit 71 in the Mueller matrix operation processing unit 21 calculates a Mueller matrix in correspondence to each pixel unit block based upon the polarization property signals provided from the discriminating unit 13. The data indicating the Mueller matrix thus calculated are saved into the Mueller matrix saving unit 72 in correspondence to the particular pixel unit block. The Mueller matrix data saved in the Mueller matrix saving unit 72 are provided to the correction matrix operation unit 74.

In the correction matrix saving unit 73, correction matrices, each set in correspondence to one of the pixel unit blocks in advance, which are used to correct the Mueller matrices having been calculated in the Mueller matrix operation processing unit 21, are saved. A correction matrix is set by measuring a test piece having known Mueller matrix values with the polarization property image measurement device 10 and comparing the measurement results with the actual Mueller matrix values. In addition, compensation data output from the compensation data acquisition unit 56 may be input to the polarizer element property correction processing unit 22 so as to set correction matrices based upon the compensation data. These correction matrices will be used to correct any error originating on the light source side.

It is desirable that the correction matrices include a matrix used to correct a Mueller matrix through multiplication, starting on the left side of the Mueller matrix, and a matrix used to correct a Mueller matrix through multiplication, starting on the right side of the Mueller matrix. A correction matrix used to correct a Mueller matrix through multiplication starting on the left side may be set so as to correct an error originating on the detection side, such as uneven polarization patterning, whereas a correction matrix used to correct a Mueller matrix through multiplication starting on the right side may be used to correct an error originating on the light source side. However, the role of the left-side multiplication matrix and the role of the right-side multiplication matrix may be reversed.

The correction matrix operation unit 74 corrects the Mueller matrix output from the Mueller matrix saving unit 72 in correspondence to each pixel unit block by multiplying the Mueller matrix by the corresponding correction matrix saved in the correction matrix saving unit 73. Through these measures, it is ensured that the polarization variable operation processing unit 2 outputs more accurate Mueller matrix values, corrected by taking into consideration the manufacturing variance among the individual polarization property image measurement devices. The Mueller matrix data resulting from the correction are provided to the display adjustment unit 23.

It is to be noted that correction may be made in correspondence to each pixel by correcting the element corresponding to the particular pixel in the Mueller matrix, instead of correcting the Mueller matrix in correspondence to each pixel unit block. In addition, while matrix multiplication is used as the correction parameter in the embodiment described above, the Mueller matrices may be corrected through other arithmetic operation processing. Furthermore, the Mueller matrix operation processing unit 21 and the polarizer element property correction processing unit 22 may be partly, or entirely disposed in the image sensor 100, preferably by enabling the signal processing chip 111 or the memory chip 112 (see FIG. 3) inside the image sensor 100 to fulfil their functions, or by laminating additional layers fulfilling these functions at lower positions relative to the signal processing chip 111 and the memory chip 112 or between the layer of the signal processing chip 111 and the layer of the memory chip 112.

Figure 6:
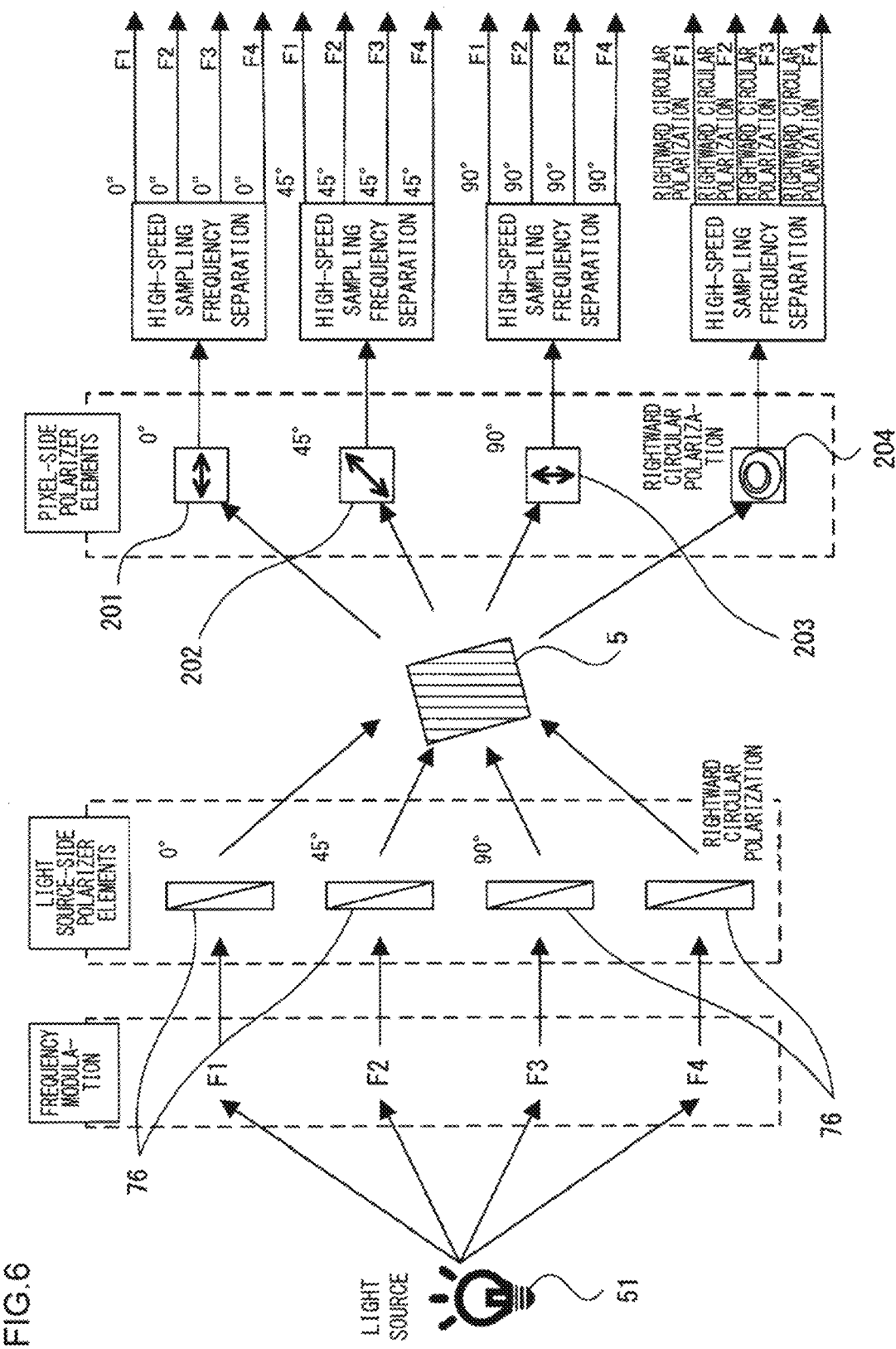
FIG. 6 is a diagram illustrating how polarization conditions may be distinguished from one another in an embodiment.

FIG. 6 schematically illustrates the 4×4 Mueller matrix measurement method adopted in the embodiment. The arrows in the figure indicate how light or pixel signals flow. A light source 51, optical elements 76, a sample 5, pixels 201 through 204, and the like different from those shown in FIG. 6 in their shapes and types may be used instead.

Light emitted from the light source 51 is split into four beams, which are individually modulated at different frequencies F1, F2, F3 and F4. The light beams, having been modulated, then undergo polarization property conversion at the optical elements 76 so as to take on a 0° polarization property, a 45° polarization property, a 90° polarization property and a rightward circular polarization property respectively. The light beams in the various polarization conditions correspond to the different frequencies. The light having been modulated is radiated onto the target object 5.

The light beams having been radiated onto the target object 5 and scattered at the target object 5 individually undergo photoelectric conversion at pixels, each of which selectively receives light in one of the four polarization conditions. A pixel 201 which selectively receives light in the polarization condition with a 0° orientation (hereafter referred to as a "0° pixel") will be indicated with a bidirectional arrow pointing to the left and the right, a pixel 202 that selectively receives light in the polarization condition with a 45° orientation (hereafter referred to as a "45° pixel") will be indicated with a bidirectional arrow on a 45° angle, a pixel 203 that selectively receives light in the polarization condition with a 90° orientation (hereafter referred to as a "90° pixel") will be indicated with a bidirectional arrow extending along the vertical direction and a pixel 204 that selectively receives light in the rightward circular polarization condition (hereafter referred to as a "rightward circular polarization pixel") will be indicated with a triple ellipsoid symbol so as to facilitate an explanation of the various embodiments below. The pixel signals indicating the various detection-side polarization conditions, having undergone the photoelectric conversion, then undergo frequency separation in correspondence to the frequencies F1, F2, F3 and F4 having been used for the intensity modulation, resulting in 4×4=16 separate elements yielded from the four types of polarization detection pixels. Through high-speed sampling of the pixel signals at the image sensor 100, a polarization property image achieving a high level of simultaneity or a polarization property video clip with a frame rate equal to or higher than 1 Hz or more desirably 10 Hz can be created.

Figure 7A:
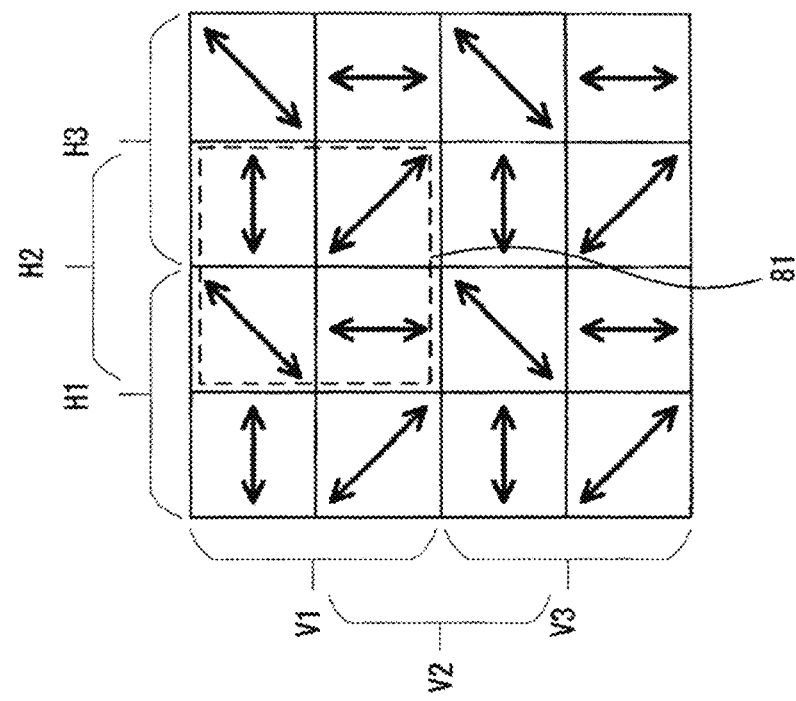
FIGS. 7A and 7B are diagrams illustrating image processing executed by adopting the pixel-shift method.
Figure 7B:
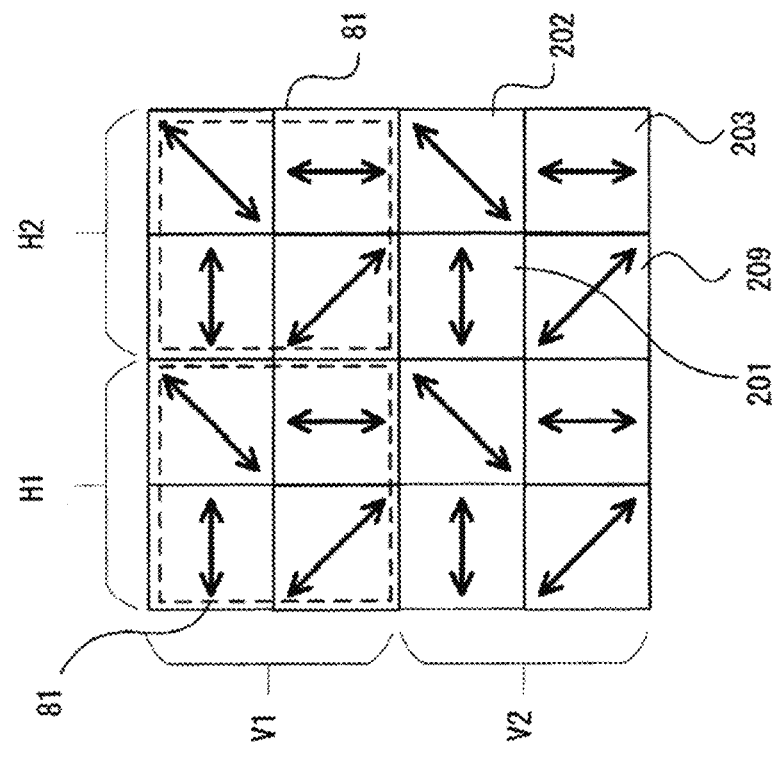

FIGS. 7A and 7B illustrate how a higher resolution may be virtually rendered through image processing. The various embodiments to be described below, having a plurality of pixels included in each pixel unit block render themselves ideal for applications in which the resolution is increased virtually. In the examples presented in FIGS. 7A and 7B, a single pixel unit block 81 is made up with pixels corresponding to four polarization conditions, i.e., 0°, 45°, 90° and 135°. In this document, a pixel 209 that selectively receives light in the polarization condition with a 135° orientation (hereafter referred to as a "135° pixel") will be indicated with a bidirectional arrow at an angle of 135°. H1, H2, H3, V1, V2 and V3 in FIGS. 7A and 7B, each represents a row or column section corresponding to a given pixel unit block.

FIG. 7A schematically illustrates a pixel arrangement in which various pixel unit blocks are disposed without any overlap with one another. In this case, a total of four pixel unit blocks 81 are each defined as a combination of either H1 or H2 and either V1 or V2. In the pixel unit block arrangement shown in FIG. 7A, four pixels correspond to a single pixel unit block 81.

FIG. 7B schematically illustrates a pixel arrangement in which pixel unit blocks 81 are set by allowing them to partially overlap with one another. In this case, a total of nine pixel unit blocks 81 are each defined by a combination of one of H1, H2 and H3 and one of V1, V2 and V3. By setting pixel unit blocks as shown in FIG. 7B so that one pixel corresponds to a single pixel unit block 81, the resolution is virtually increased by a factor of four over the resolution achieved in conjunction with the pixel unit block arrangement shown in FIG. 7A.

The pixel arrangement with pixel unit blocks 81 set to partially overlap one another, improves the resolution as perceived by the viewer in polarization property image measurement. In particular, it is desirable to set pixel unit blocks 81, each made up with a plurality of pixels, so that each pair of pixel unit blocks 81 adjacent to each other are offset relative to each other by an extent equivalent to one pixel along the horizontal direction or the vertical direction.

Figure 8:
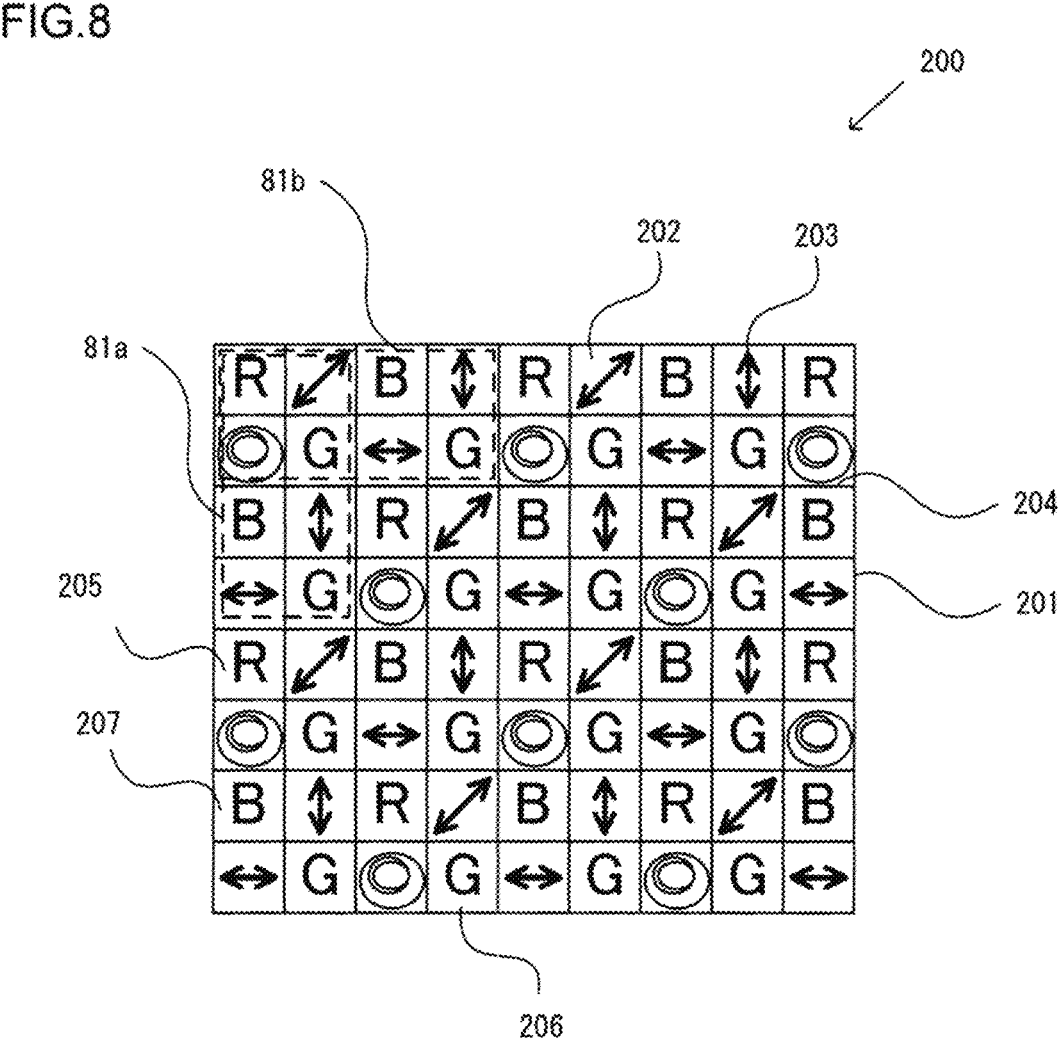
FIG. 8 shows an example of a pixel array that may be adopted at an image-capturing surface in the first embodiment.

FIG. 8 schematically illustrates part of the pixel array at an image-capturing surface 200 of the image sensor 100 in the polarization property image measurement device 10 achieved in the embodiment. The image sensor 100 in the polarization property image measurement device 10 in the embodiment includes pixels 205 through 207, each of which selectively receives red color light, green-color light or blue-color light, in addition to the polarization detection pixels 201 through 204, each of which receives a light beam in the 0° polarization condition, the 45° polarization condition, the 90° polarization condition or the rightward circular polarization condition.

It is to be noted that any combination of color pixels, each of which selectively receives light in a given wavelength range, may be adopted, as long as colors that need to be used in a color image can be reproduced as a result of analysis.

A pixel 205 that selectively receives red-color light (hereafter referred to as an "R pixel") will be indicated with the letter "R", a pixel 206 that selectively receives green-color light (hereafter referred to as a "G pixel") will be indicated with the letter "G", and a pixel 207 that selectively receives blue-color light (hereafter referred to as a "B pixel") will be indicated with the letter "B" so as to facilitate the subsequent explanation of the various embodiments. In the embodiment, R pixels each include a color filter through which red-color light is selectively transmitted, G pixels each include a color filter through which green-color light is selectively transmitted and B pixels each include a color filter through which blue-color light is selectively transmitted, all disposed on the light-entry side of the photoelectric conversion units 62 at the respective color pixels.

A pixel unit block 81*a* in the image sensor 100 is configured with four polarization detection pixels 201 through 204 corresponding to the four different polarization conditions, one R pixel 205, two G pixels 206 and one B pixel 207. Each pixel unit block 81*a* corresponds to a particular position at the target object or the background (hereafter referred to as a photographic subject). A 4×4 Mueller matrix corresponding to the particular position is obtained based upon pixel signals output from the four polarization detection pixels 201 through 204 included in the pixel unit block 81*a*. In addition, color image information corresponding to the particular position is obtained based upon pixel signals output from the color pixels included in the pixel unit block 81*a*. It is desirable that pixel unit blocks 81*a* be defined with an offset relative to one another by an extent equivalent to a single pixel so that they overlap one another through the pixel-shift method described earlier in order to improve the perceived resolution.

It is to be noted that pixel unit blocks may be set with an arrangement other than that described above, as long as all the pixels present at the image-capturing surface 200 are included in the pixel unit blocks. For instance, pixel unit blocks may be set so that each includes two pixels (down)× four pixels (across) as indicated by the dotted line rectangle 81*b* in FIG. 8, instead of setting pixel unit blocks so that each includes four pixels (down)×two pixels (across) as indicated by the dotted line rectangle 81*a* in FIG. 8. The present invention is in no way limited to the pixel arrangements assumed at the image-capturing surface 200 in the various embodiments described below, and any pixel arrangement may be adopted, as long as polarization detection pixels corresponding to all polarization conditions and color pixels, which are needed on the detection side in the various embodiments, are disposed so that a measurement target area of the target object 5 can be analysed at a desired resolution.

Figure 9:
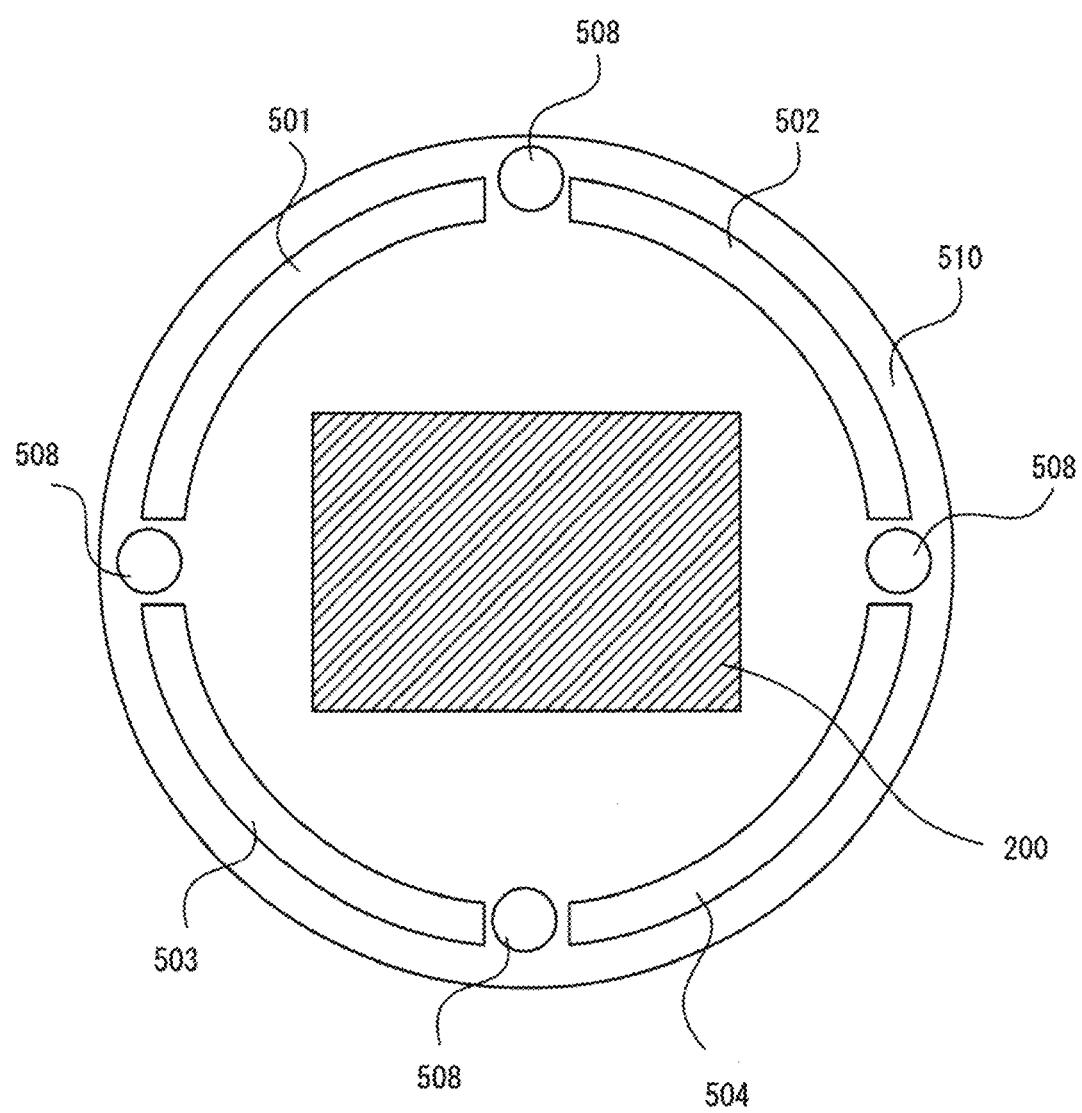
FIG. 9 shows an example of a structure that may be adopted for an objective unit in the first embodiment.

FIG. 9 illustrates the positional arrangement with which the image-capturing surface 200 and radiation ports 501 through 504 and 508 are disposed at an objective unit 510 that faces opposite the target object 5, in the polarization property image measurement device 10 in the embodiment. The objective unit 510 in the polarization property image measurement device 10 is designed as a compact unit, which enables image-capturing in narrow areas, with the radiation ports 501 through 504 and 508 disposed close to one another and set in close proximity to the image-capturing surface 200. This means that the polarization property image measurement device 10 in the embodiment is ideal in applications in image-capturing devices that include a contact image sensor or the like such as an endoscope.

Light beams in the various polarization conditions, having undergone intensity modulation at different frequencies F1, F2, F3 and F4, are radiated through the four radiation ports 501 through 504 respectively. The light beam in the 0° polarization condition, having undergone intensity modulation at the frequency F1, is radiated through the first radiation port 501. The light beam in the 45° polarization condition, having undergone intensity modulation at the frequency F2, is radiated through the second radiation port 502. The light beam in the 90° polarization condition, having undergone intensity modulation at the frequency F3, is radiated through the third radiation port 503. The light beam in the rightward circular polarization condition, having undergone intensity modulation at the frequency F4, is radiated through the fourth radiation port 504. Through white light radiation ports 508, each disposed at one of four different locations, un-polarized white light, having undergone intensity modulation at a frequency F5, different from the frequencies of the radiated light beams in the various polarization conditions, is radiated. The un-polarized white light beams radiated through the white light radiation ports 508 undergo intensity modulation so as to make it possible to extract components (frequencies F1 through F4) having originated from the radiated light beams in the various polarization conditions by separating the frequency component (frequency F5) having originated in the white light after scattered white light is received at the polarization detection pixels.

At the image-capturing surface 200, disposed at a central area of the objective unit 510, the polarization detection pixels and the color pixels are arrayed by adopting a specific pattern such as that shown in FIG. 8.

It is to be noted that the present invention may be adopted in conjunction with radiation ports and an image-capturing surface disposed at the objective unit 510 in positional arrangements and quantities other than those in the various embodiments described below, as long as light beams in all the polarization conditions required in the embodiments can be radiated onto the target object and the light beams scattered at the target object can be detected at the image-capturing surface.

Figure 10:
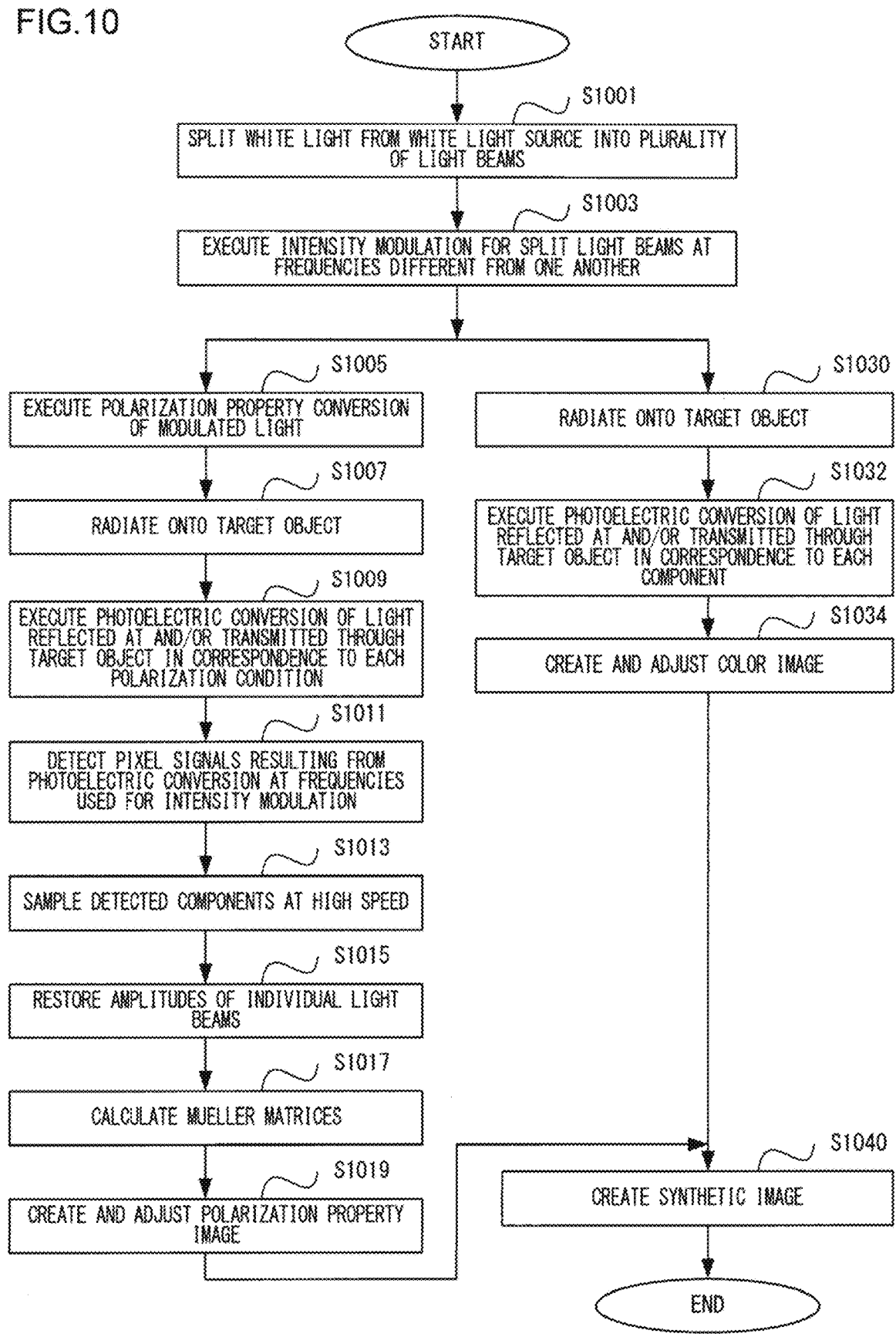
FIG. 10 is a flowchart of the polarization property image creation processing executed in the first embodiment.

FIG. 10 presents a flowchart of a polarization property image measurement method executed in the polarization property image measurement device 10 in the embodiment.

In step S1001, the light source radiating unit 11 splits light originating from the white light source into a plurality of light beams via a beam splitter or the like. Once the white light has been split, the operation proceeds to step S1003. In step S1003, the light source radiating unit 11 executes intensity modulation for the individual light beams at frequencies different from one another. For assigning a specific polarization condition to each of the light beams having undergone the intensity modulation, the operation proceeds to step S1005, whereas for using the individual light beams having undergone the intensity modulation for creation of a color image, the operation proceeds to step S1030.

In step S1005, the light source radiating unit 11 executes the polarization property conversion of the light beams having undergone the intensity modulation in step S1003, via polarizers and/or phase shifters. Once the polarization property conversion is completed, the operation proceeds to step S1007. In step S1007, the light source radiating unit 11 radiates light beams assuming various polarization conditions resulting from the polarization property conversion onto the target object. Once the light beams have been radiated onto the target object 5, the operation proceeds to step S1009.

In step S1009, the image-capturing unit 12 engages the polarization detection pixels at the image sensor 100 in photoelectric conversion of light scattered from the target object 5 in correspondence to each of the various polarization conditions. Once the photoelectric conversion is completed, the operation proceeds to step S1011. In step S1011, the discriminating unit 13 detects pixel signals resulting from the photoelectric conversion at the frequencies with which the intensity modulation has been executed. Once the pixel signals are detected, the operation proceeds to step S1013.

In step S1013, the discriminating unit 13 executes high-speed sampling of components of the detected pixel signals. Once the high-speed sampling of the pixel signal components is completed, the operation proceeds to step S1015. In step S1015, the Mueller matrix operation processing unit 21 restores the amplitudes of light beams in the various polarization conditions, which are needed for Mueller matrix calculation, from the pixel signals output from the discriminating unit 13, i.e., from polarization property signals. Once the amplitudes have been restored, the operation proceeds to step S1017.

In step S1017, the Mueller matrix operation processing unit 21 calculates Mueller matrices based upon the restored amplitudes. In addition, the Mueller matrices are corrected by the polarizer element property correction processing unit 22 as needed. Once the Mueller matrices are obtained, the operation proceeds to step S1019. In step S1019, the display adjustment unit 23 creates and adjusts a polarization property image based upon the Mueller matrices having been obtained as described above. Once a polarization property image has been prepared and adjusted, the operation proceeds to step S1040.

A color image is created by first radiating light having undergone intensity modulation via the light source radiating unit 11 onto the target object 5 in step 1030. Once the light, having undergone the intensity modulation, has been radiated onto the target object 5, the operation proceeds to step S1032. In step S1032, the image-capturing unit 12 engages the color pixels each corresponding to a specific color at the image sensor 100 in photoelectric conversion of light scattered from the target object 5. Once the photoelectric conversion is completed, the operation proceeds to step S1034. In step S1034, the color image creation processing unit 41 creates a color image based upon the pixel signals resulting from the photoelectric conversion and the color image display adjustment unit 42 adjusts the color image so as to render it ready to be combined with the polarization property image. Once the color image has been adjusted, the operation proceeds to step S1040.

In step S1040, the image synthesis processing unit 43 combines the polarization property image and the color image having been obtained so as to create a synthetic image. Once a synthetic image has been obtained, the processing ends.

The following advantages and operations are achieved through the first embodiment described above.

(1) The polarization property image measurement device 10 in the embodiment comprises the light source radiating unit 11 that executes intensity modulation for a plurality of light beams, assuming polarization conditions different from one another, at frequencies each different from others, and radiates the light beams having undergone the intensity modulation onto a target object, the image sensor 100 having disposed thereat a plurality of polarization detection pixels 201 through 204 at each of which light having been radiated from the light source radiating unit 11 onto the target object 5 and scattered at the target object 5 assuming a polarization condition different from others, undergoes photoelectric conversion, and the discriminating unit 13 that detects signals individually output from the plurality of polarization detection pixels 201 through 204 at the different frequencies, differentiates each signal from other signals as a signal originating from a light beam in one polarization condition different from the other polarization conditions and outputs differentiated signals. The polarization property image measurement device 10 structured as described above is thus able to analyse a plurality of light beams assuming different polarization conditions, simultaneously radiated from a plurality of radiating units or radiated through multiplexing, by separating them from one another.

(2) The light source radiating unit 11 in the polarization property image measurement device 10 achieved in the embodiment simultaneously radiates light beams assuming polarization conditions different from one another, and the image sensor 100 concurrently detects signals individually output from the plurality of polarization detection pixels 201 through 204. The polarization property image measurement device 10 is thus able to simultaneously obtain polarized light data corresponding to polarization conditions different from one another, which express a single polarization property image. In other words, a polarization property image achieving a high level of simultaneity can be obtained. In addition, this feature makes it possible to achieve improvements in the frame rate and the exposure time over those achieved in a structure in which light beams are radiated in sequence.

(3) The image sensor 100 in the polarization property image measurement device 10 achieved in the embodiment further includes a plurality of color pixels 205 through 207 at which visible light departing the target object 5 undergoes photoelectric conversion and a visible image creation unit that generates an image of the target object 5 based upon signals individually output from the plurality of color pixels 205 through 207. This structural feature enables the polarization property image measurement device 10 to generate a high quality image that can be viewed by the user with ease by combining the polarization property image and the color image.

(4) The polarization property image measurement device 10 in the embodiment further includes white light radiation ports 508 through which white light is radiated onto the target object, and the image sensor 100 further includes color filters disposed on the light entry side of the individual color pixels 205 through 207. These structural features make it possible to create a color image without having to demodulate pixel signals for purposes of color image creation.

(5) The polarization property image measurement device 10 achieved in the embodiment includes the white light radiation ports 508 through which white light having undergone intensity modulation at a frequency for visible image creation, different from the various frequencies used in the intensity modulation described above, is radiated onto the target object 5. This structural feature makes it possible to separate the component of the white light from the light received at the polarization property pixels 201 through 204.

(6) The polarization property image measurement device 10 achieved in the embodiment further includes the display adjustment unit 23 that generates a polarization property image or a synthetic image expressing the physical properties of the target object 5 based upon the signals differentiated via the discriminating unit 13. As a result, the physical properties of the target object 5 can be examined or part of the target object 5 can be distinguished from the remaining part of the target object 5 based upon a change in the physical properties of the target object 5.

(7) The polarization property image measurement device 10 achieved in the embodiment includes a processing circuit 111 disposed in correspondence to each of the pixels at the image sensor 100 to process a signal output from the pixel. The processing circuit 111 and the discriminating unit 13 are disposed in a layer different from an image-capturing layer 113, in correspondence to each of the plurality of polarization detection pixels 201 through 204. Through these measures, it is ensured that the various components in the individual pixel signals can be simultaneously detected with high accuracy.

(8) The polarization property image measurement device 10 in the embodiment is ideal in applications in image-capturing devices such as a camera, a microscope, and an endoscope. The image-capturing device equipped with the polarization property image measurement device 10 can be provided as a compact unit capable of polarization measurement achieving a high level of simultaneity.

The following variation is also within the scope of the present invention, and the variation may be adopted in combination with the embodiment described above.

(Variation 1)

While the plurality of light beams having passed through the optical property conversion unit 54 are transmitted through different optical fibers and are radiated individually through the different radiation ports 501 through 504 and 508 at the light source radiating unit 11 in the polarization property image measurement device 10 in the embodiment described above, a plurality of light beams may be transmitted through a single optical fiber through polarization multiplexing and be radiated through the plurality of radiation ports 501 through 504 and 508. In such a case, the transmission unit 55 can be configured with a thin tube and the polarization property image measurement device 10 can be provided as an even more compact unit.

Second Embodiment

While a polarization property image measurement device 20 achieved in the second embodiment adopts a structure similar to that of the polarization property image measurement device 10 in the first embodiment, it adopts a color image creation method different from that in the first embodiment. Components identical to those in the first embodiment are assigned with the same reference signs as those in the first embodiment so as to preclude, wherever possible, the necessity for a repeated explanation thereof.

Figure 11:
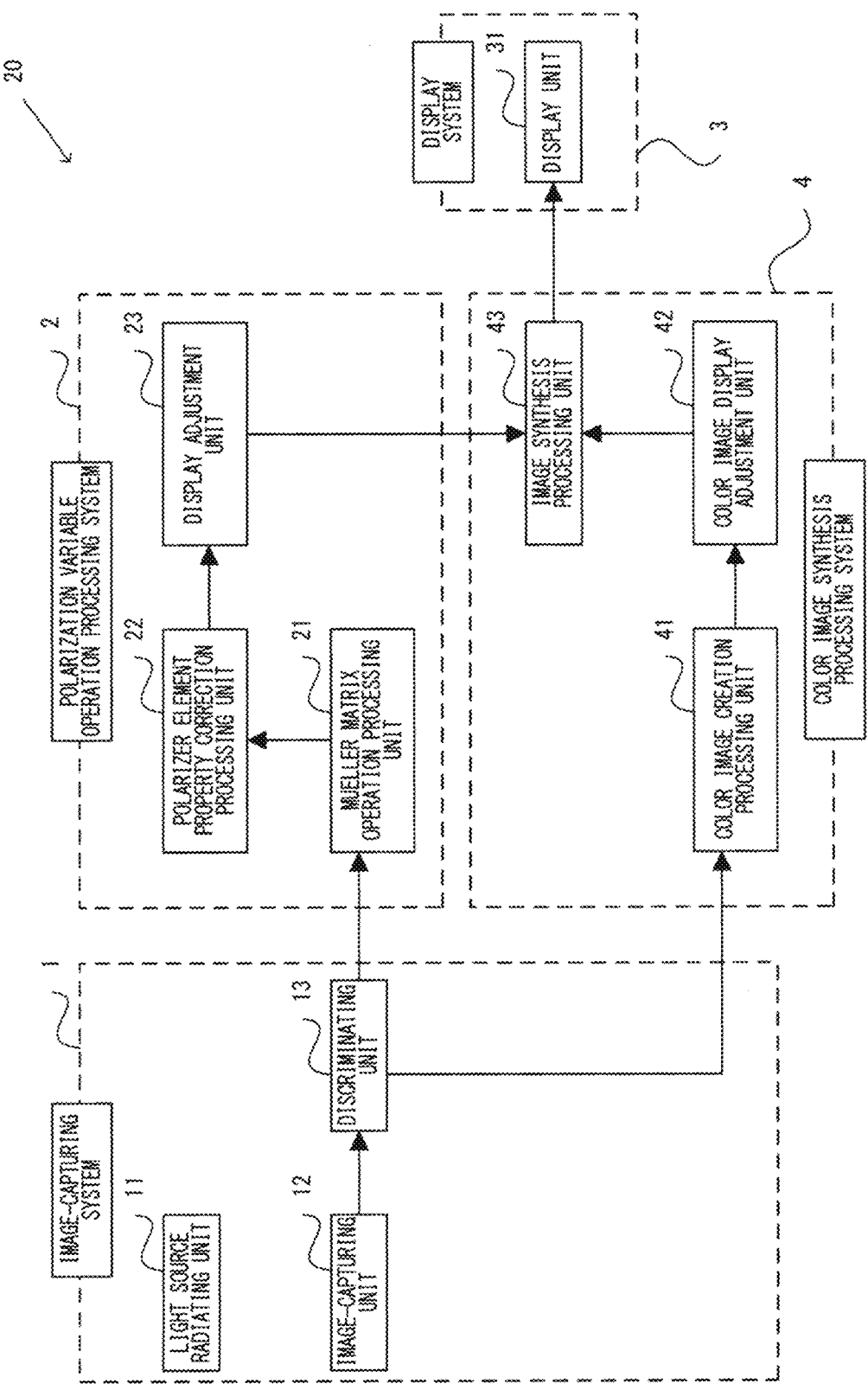
FIG. 11 is a schematic block diagram pertaining to a polarization property image measurement device achieved in a second embodiment.

FIG. 11 is a diagram showing the functional blocks in the polarization property image measurement device 20 achieved in the second embodiment. While the functional blocks in the polarization property image measurement device 20 are configured substantially identically to the functional blocks in the polarization property image measurement device 10 in the first embodiment (see FIG. 1), the polarization property image measurement device 20 is distinguishable in that pixel signals output from the color pixels need to be differentiated at the discriminating unit 13.

Figure 12:
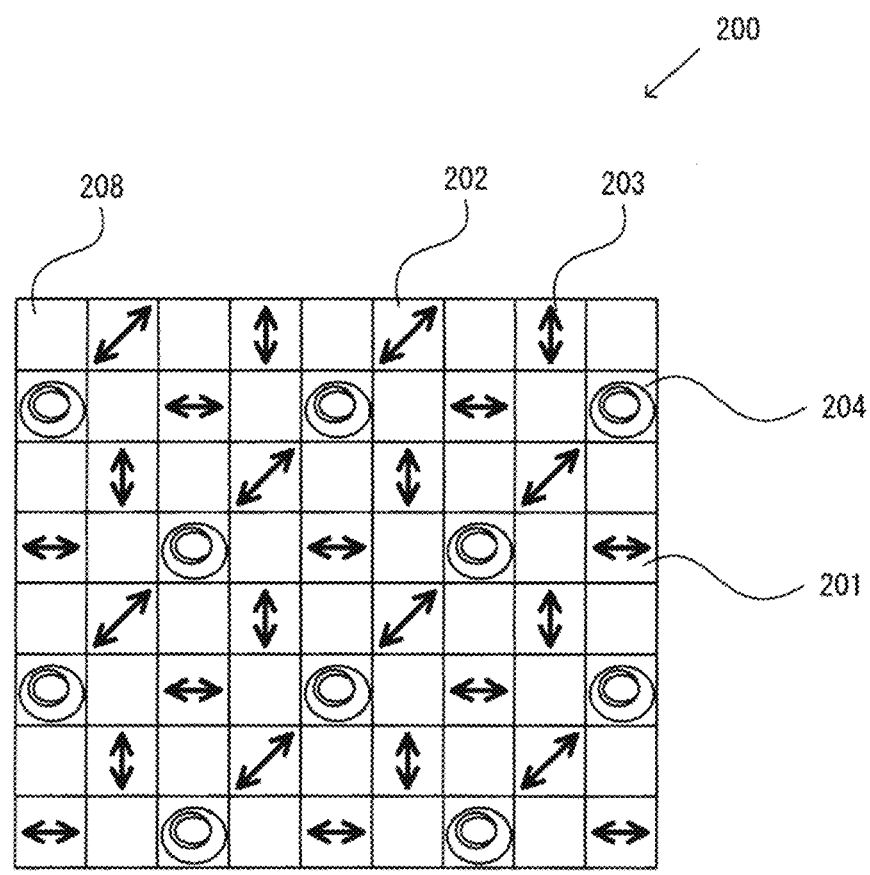
FIG. 12 shows an example of a pixel array that may be adopted at the image-capturing surface in the second embodiment.

FIG. 12 schematically illustrates part of the pixel array at the image-capturing surface 200 of the image sensor 100 in the polarization property image measurement device 20 achieved in the second embodiment. Pixels 201 through 204, each of which selectively receives a light beam in a specific polarization condition among the 0° polarization condition, the 45° polarization condition, the 90° polarization condition and the rightward circular polarization condition, and pixels 208, are disposed at the image-capturing surface 200, with no visible light range filters such as color filters, disposed on the light-entry side of the photoelectric conversion units 62 of the pixels 208.

Figure 13:
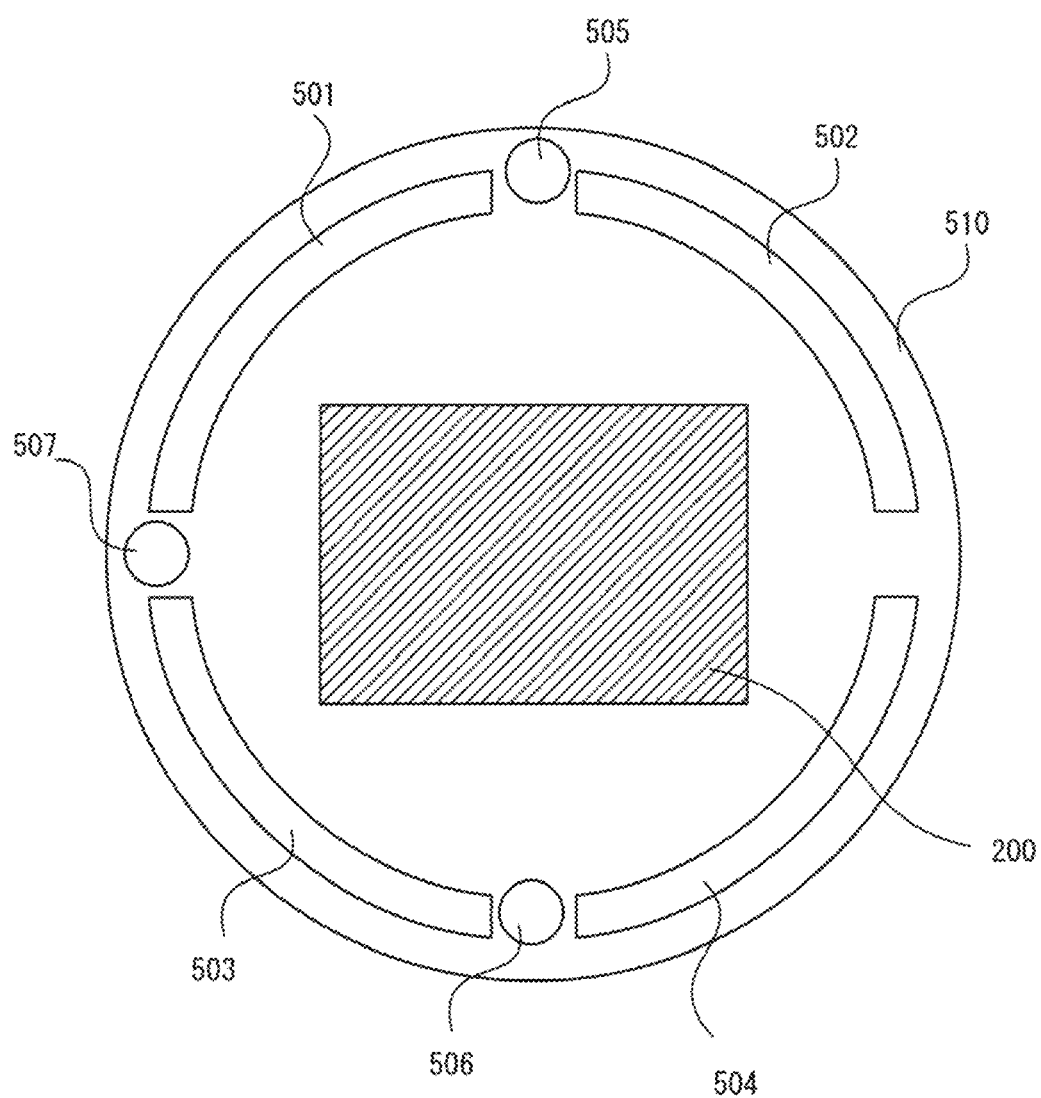
FIG. 13 shows an example of a structure that may be adopted for the objective unit in the second embodiment.

FIG. 13 illustrates the positional arrangement with which the radiation ports 501 through 507 and the image-capturing surface 200 are disposed at the objective unit 510, which faces opposite the target object 5 in the polarization property image measurement device 20 in the embodiment.

Light beams in the various polarization conditions, having undergone intensity modulation at different frequencies F1, F2, F3 and F4, are radiated through the four radiation ports 501 through 504 at the polarization property image measurement device 20 in the embodiment, as in the polarization property image measurement device 10 in the first embodiment. Red-color light, having undergone intensity modulation executed at a frequency F6 different from the frequencies F1, F2, F3 and F4, is radiated through a red-color light radiation port 505. Green-color light having undergone intensity modulation executed at a frequency F7 different from the frequencies F1, F2, F3, F4 and F6, is radiated through a green-color light radiation port 506. Blue-color light, having undergone intensity modulation executed at a frequency F8 different from the frequencies F1, F2, F3, F4, F6 and F7, is radiated through a blue-color light radiation port 507.

At the image-capturing surface 200, disposed at a central area of the objective unit 510, the polarization detection pixels 201 through 204 and the color pixels 208 without wavelength filters are arrayed by adopting a specific pattern such as that shown in FIG. 12.

In the polarization property image measurement device 20 achieved in the embodiment, color filters are not used. Instead, red-color light, green-color light and blue-color light are differentiated through intensity modulation and demodulation executed by using different frequencies, each set in correspondence to a specific color of light, in much the same way as light beams are differentiated in correspondence to the various polarization conditions.

Figure 14:
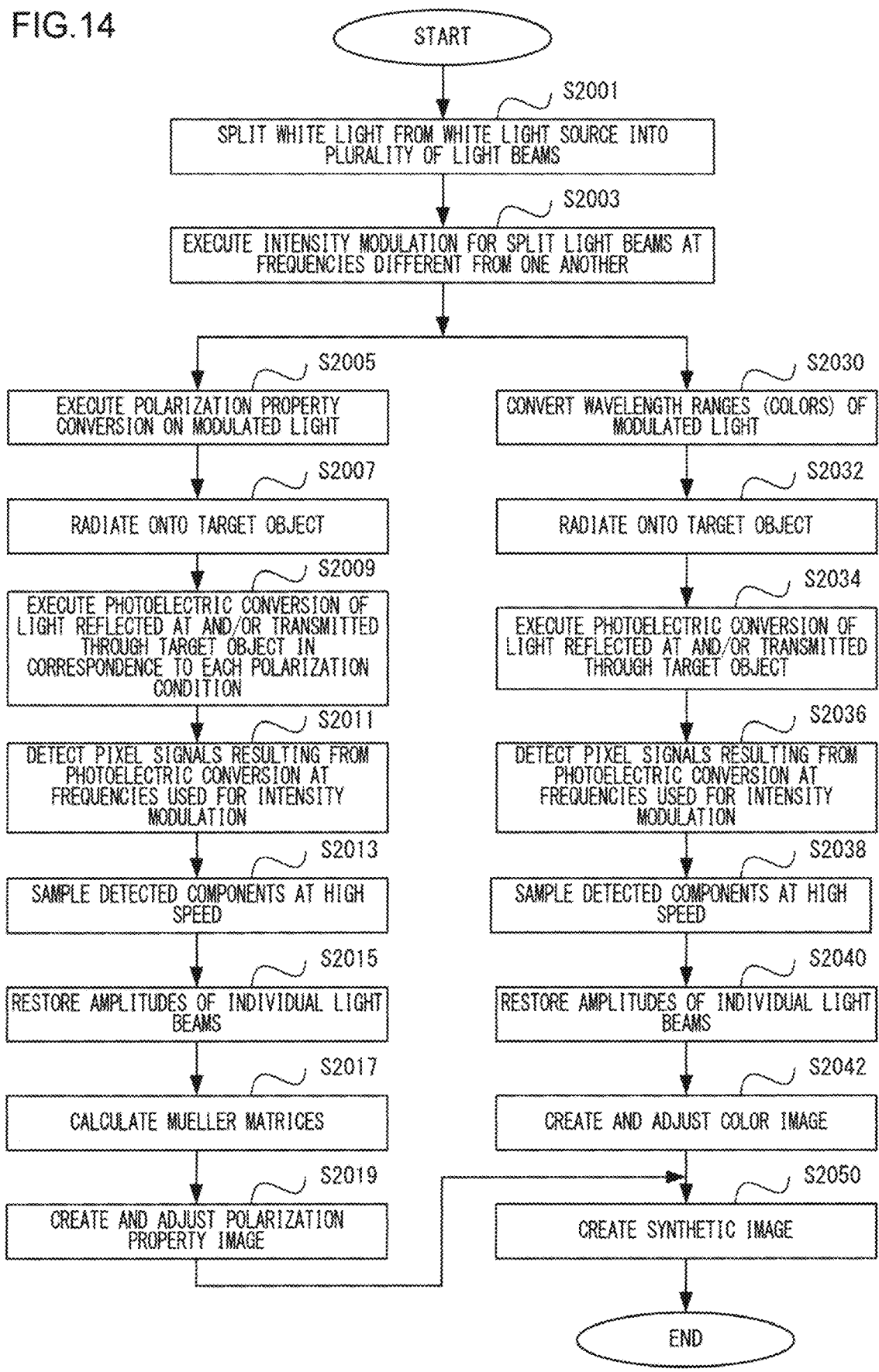
FIG. 14 is a flowchart of the polarization property image creation processing executed in the second embodiment.

FIG. 14 presents a flowchart of a polarization property image measurement method adopted in the polarization property image measurement device 20 in the embodiment. The processing pertaining to polarization property image creation, executed in step S2001 through step S2019 (corresponds to steps S1001 through S1019 in FIG. 10) and the processing pertaining to synthetic image creation executed in step S2050 (corresponds to step S1040 in FIG. 10) are identical to those executed in the first embodiment, and a repeated explanation is not provided.

In step S2030, the light source radiating unit 11 converts three white light beams having undergone the intensity modulation in step S2003 into light beams in three colors assuming different wavelength ranges from one another. Once light beams in three different colors have been obtained, the operation proceeds to step S2032. In step S2032, the light source radiating unit 11 radiates light beams in the three colors onto the target object. Once the light beams in three different colors are radiated, the operation proceeds to step S2034.

In step S2034, light scattered at the target object 5 undergoes photoelectric conversion at the color pixels 208 in the image sensor 100 of the image-capturing unit 12 and pixel signals are thus generated. Once the photoelectric conversion is completed, the operation proceeds to step S2036. In step S2036, the discriminating unit 13 detects the pixel signals resulting from the photoelectric conversion with the frequencies at which the intensity modulation has been executed. Once the detection is completed, the operation proceeds to step S2038.

In step S2038, the discriminating 13 executes high-speed sampling of the detected signals containing the various color components. Once the high-speed sampling is completed, the operation proceeds to step S2040. In step S2040, the color image creation processing unit 41 restores the amplitudes of the light beams with which the image has been captured based upon the individual color components in the pixel signals having been separated. Once the amplitudes have been restored, the operation proceeds to step S2042.

In step S2042, the color image creation processing unit 41 creates a color image by using information pertaining to the restored amplitudes of the individual light beams. In addition, the color image display adjustment unit 42 adjusts the color image in order to render it ready to be combined with the polarization property image. Once the color image has been adjusted, the operation proceeds to step S2050.

In addition to the advantages and operations achieved through the first embodiment, the following advantage and operation are realized through the second embodiment described above.

(1) The polarization property image measurement device 20 in the embodiment includes the light source radiating unit 11 that radiates various light beams emitted from a plurality of color light sources corresponding to colors assuming wavelength ranges different from one another, onto a target object after executing intensity modulation at a plurality of frequencies set for a plurality of visible image creation, all different from the various frequencies set for polarization measurement light beams. As a result, a color image can be created based upon pixel signals output from color pixels of a single type.

The following variation is also within the scope of the present invention, and the variation may be adopted in combination with the embodiment described above.

(Variation 1)

While light beams to be radiated for purposes of polarization property image creation and light beams to be radiated for purposes of color image creation are generated by splitting light emitted from a single light source in the light source radiating unit 11 at the polarization property image measurement device 20 achieved in the embodiment, light beams to be radiated for purposes of color image creation may be output from a plurality of light sources constituted with a plurality of monochromatic LEDs or the like. Through these measures, the various types of radiated light beams and, more specifically, the light beams radiated for purposes of polarization property image creation and the light beams radiated for purposes of color image creation can be controlled more independently of each other than in previous examples and, as a result, more optimal image-capturing conditions can be selected.

Third Embodiment

A polarization property image measurement device 30 achieved in the third embodiment adopts a structure similar to that of the polarization property image measurement device 10 in the first embodiment. It is, however, distinguishable from the polarization property image measurement device 10 in the first embodiment in that a greater variety of pixels compared to the first embodiment are disposed at two image-capturing surfaces and in that a polarization property image and a color image are created by taking advantage of the parallax effect. Components identical to those in the first embodiment are assigned with the same reference signs as those in the first embodiment so as to preclude the necessity for a repeated explanation thereof wherever possible.

Figure 15:
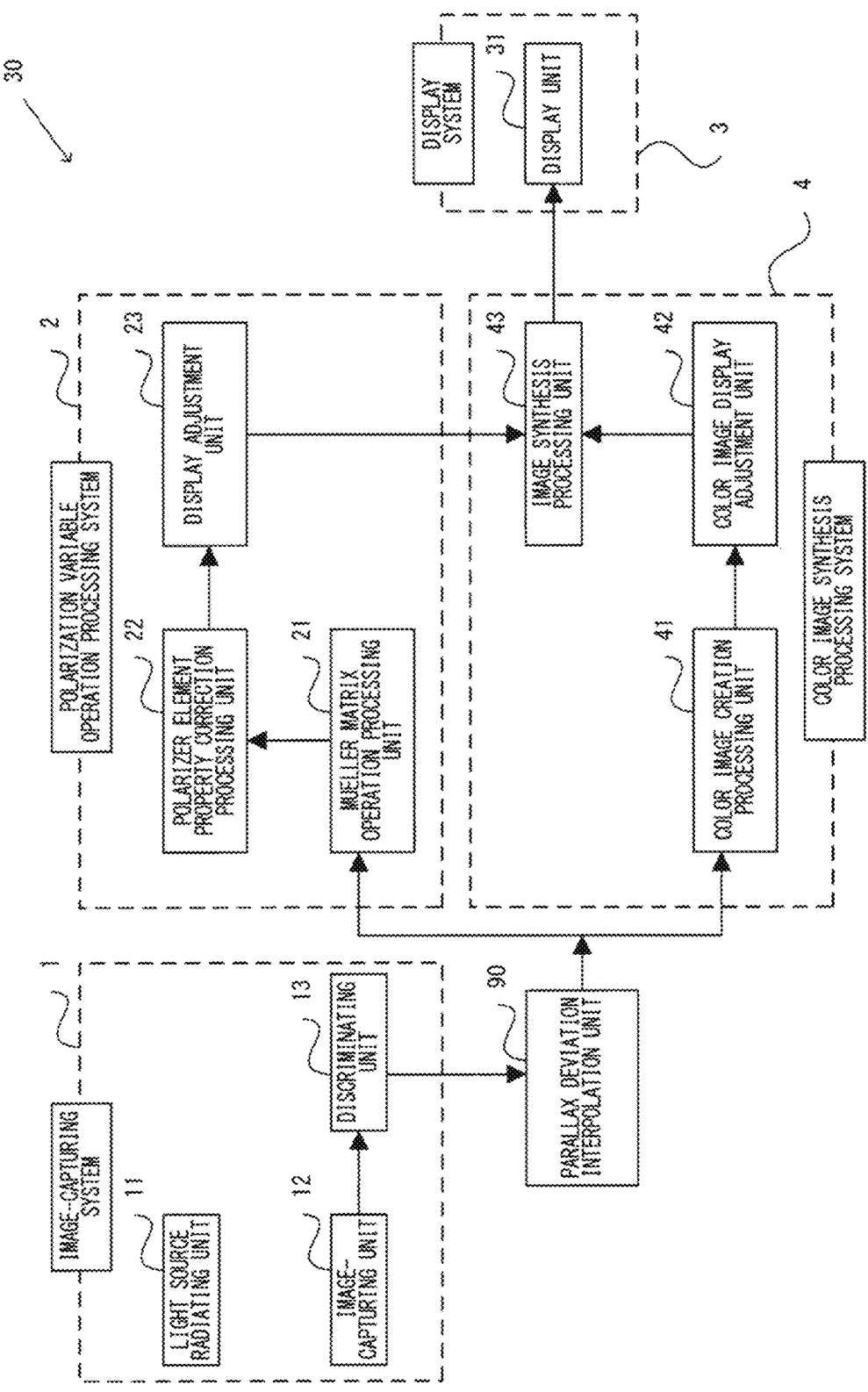
FIG. 15 is a schematic block diagram pertaining to a polarization property image measurement device achieved in a third embodiment.

FIG. 15 is a diagram showing the functional blocks in the polarization property image measurement device 30 achieved in the third embodiment. The functional blocks in the polarization property image measurement device 30 are configured substantially identically to the functional blocks in the polarization property image measurement device 10 in the first embodiment (see FIG. 1). The third embodiment is distinguishable in that after the pixel signals output from the polarization property pixels are differentiated, the polarization property signals resulting from the differentiation at the discriminating unit 13 and color image signals are analysed at a parallax deviation interpolation unit 90. It is also distinguishable in that a three-dimensional color image and a synthetic three-dimensional image are generated in the color image synthesis processing system 4.

The parallax deviation interpolation unit 90 interpolates pixel information by using parallax indicated by sets of pixel information obtained at two image-capturing surfaces 200 in the objective unit 510 of the polarization property image measurement device 30 and also analyses information pertaining to the parallax. It then provides the interpolation results and the analysis results to the color image synthesis processing system 4.

Figure 16:
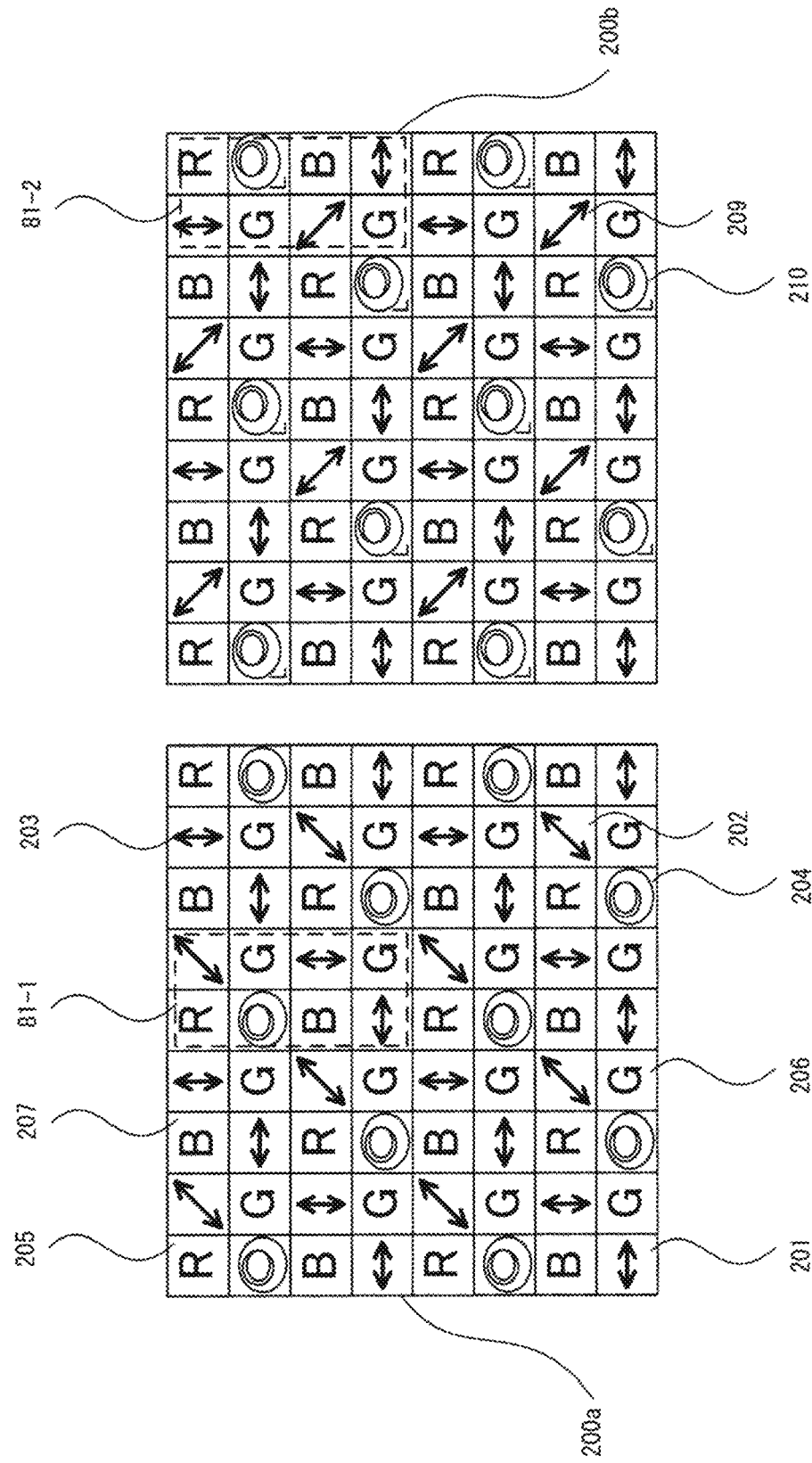
FIG. 16 shows an example of a pixel array that may be adopted at the image-capturing surface in the third embodiment.

FIG. 16 schematically illustrates part of the pixel arrays at two image-capturing surfaces 200a and 200b of the image sensor 100 in the polarization property image measurement device 30 achieved in the third embodiment. Light having departed the photographic subject from various positions thereupon is received at the image-capturing surface 200a and the image-capturing surface 200b at different angles of incidence. At the image-capturing surface 200a and the image-capturing surface 200b, pixels 201 through 204, 209 and 210 at which light beams in the 0° polarization condition, the 45° polarization condition, the 90° polarization condition, the rightward circular polarization condition, the 135° polarization condition, and the leftward circular polarization condition are selectively received, R pixels 205, G pixels 206 and B pixels 207 are disposed. The 45° pixels 202 and the rightward circular polarization pixels 204 are disposed only at the image-capturing surface 200a. The 135° pixels 209 and the pixels 210 that selectively receive the leftward circularly polarized light (hereafter referred to as leftward circular polarization pixels) are disposed only at the image-capturing surface 200b. The leftward circular polarization pixels are each indicated with a mark created by flipping the mark used to indicate the rightward circular polarization pixels 204 to reverse the left and right sides and appending the letter "L".

At the image-capturing surface 200a and the image-capturing surface 200b, different types of pixels can be disposed at matching pixel positions within the respective image-capturing surfaces. Namely, at matching pixel positions within the two image-capturing surfaces, polarization detection pixels that selectively receive light beams in different polarization conditions, among the polarization detection pixels 201 through 204, 209 and 210, may be disposed or color pixels corresponding to different colors may be disposed. In the example presented in FIG. 16, a 135° pixel is disposed within the image-capturing surface 200b at a relative pixel position that matches a relative pixel position at which a 45° pixel is disposed within the image-capturing surface 200a. In addition, a leftward circular polarization pixel is disposed within the image-capturing surface 200b at a relative pixel position matching a relative pixel position at which a rightward circular polarization pixel is disposed within the image-capturing surface 200a.

The parallax deviation interpolation unit 90 interpolates pixel information based upon a deviation attributable to the parallax effect between the pixel information obtained via the image-capturing surface 200a and the pixel information obtained via the image-capturing surface 200b. The parallax deviation interpolation unit 90 restores the amplitudes of light beams in the various polarization conditions, each defined by a specific combination of a radiation-side polarization condition and a detection-side polarization condition. Based upon the amplitudes of the light beams in the various polarization conditions thus restored, the parallax deviation interpolation unit 90 calculates the deviation of the pixel information obtained via the image-capturing surface 200a and the pixel information obtained via the image-capturing surface 200b relative to each other, which is attributable to the parallax effect. Based upon the calculated parallax deviation, attributable to the parallax effect, the parallax deviation interpolation unit 90 determines corresponding pixel unit blocks 81-1 and 81-2 at the image-capturing surface 200a and the image-capturing surface 200b, at which light beams having departed the same position of the target object 5 are to undergo photoelectric conversion.

It is to be noted that the parallax deviation interpolation unit 90 may determine deviation between the image-capturing surface 200a and the image-capturing surface 200b attributable to the parallax effect, based upon pixel information output from the color pixels. As an alternative, the parallax deviation interpolation unit 90 may determine deviation attributable to the parallax effect based upon polarization property images created on a temporary basis by using the two sets of pixel information. Such temporary images may be created by skipping display adjustment and the like, as long as deviation attributable to the parallax effect can be calculated based upon the images.

In the example presented in FIG. 16, the unit pixel block 81-1 at the image-capturing surface 200a and the unit pixel block 81-2 at the image-capturing surface 200b are determined, through the calculation of the deviation attributable to the parallax effect executed by the parallax deviation interpolation unit 90, to be corresponding pixel unit blocks in which light beams, having departed the same position of the target object, undergo photoelectric conversion. In this situation, all the polarization conditions (six different polarization conditions in this example) assumed in the light beams received in the two pixel unit blocks can be used in Mueller matrix calculation in correspondence to the particular position at the target object, and in particular, in the calculation of Stokes vector components during the Miller matrix calculation process.

The third component S3 (refer to the expression (2)) of the Stokes vector can be determined based upon the difference between the light intensity of light polarized along the 45° direction and the light intensity of light polarized along the 135° direction. While information on the 135° polarization condition can be obtained through polarization measurement of light beams in the 0° polarization condition, the 45° polarization condition and the 90° polarization condition (refer to the expression (4)), more accurate data can be obtained by directly measuring light in the 135° polarization condition.

The fourth component S4 (refer to the expression (2)) of the Stokes vector can be determined based upon the difference between the light intensity of leftward circularly polarized light and the light intensity of rightward circularly polarized light. While information on the leftward circular polarization condition can be obtained through polarization measurement of light beams in the 0° polarization condition, the 90° polarization condition and the rightward circular polarization condition (refer to the expression (4)), more accurate data can be obtained by directly measuring light in the leftward circular polarization condition.

The parallax deviation interpolation unit 90 outputs the data having been obtained for purposes of Mueller matrix calculation to the Mueller matrix operation processing unit 21.

It is to be noted that pixels corresponding to the various polarization conditions can be disposed by adopting any suitable positional arrangement as long as Mueller matrices or Stokes vector components can be calculated as required.

In addition, the parallax deviation interpolation unit 90 outputs information on deviation, attributable to the parallax effect, between the color pixel information obtained via the image-capturing surface 200a and the color pixel information obtained via the image-capturing surface 200*b* to the color image creation processing unit 41.

The color image creation processing unit 41 in the polarization property image measurement device 30 achieved in the embodiment creates a three-dimensional color image based upon the parallax information provided by the parallax deviation interpolation unit 90. The three-dimensional color image having been created is then output to the color image display adjustment unit 42. The color image display adjustment unit 42 adjusts the three-dimensional color image so as to render it ready for display and outputs the adjusted three-dimensional color image to the image synthesis processing unit 43. The image synthesis processing unit 43 correlates the three-dimensional image input thereto from the color image display adjustment unit 42 with the polarization property image input thereto from the display adjustment unit 23 based upon the parallax information and maps the two-dimensional polarization property image upon the three-dimensional image. The image synthesis processing unit 43 outputs the synthetic three-dimensional image thus obtained to the display unit 31.

Figure 17:
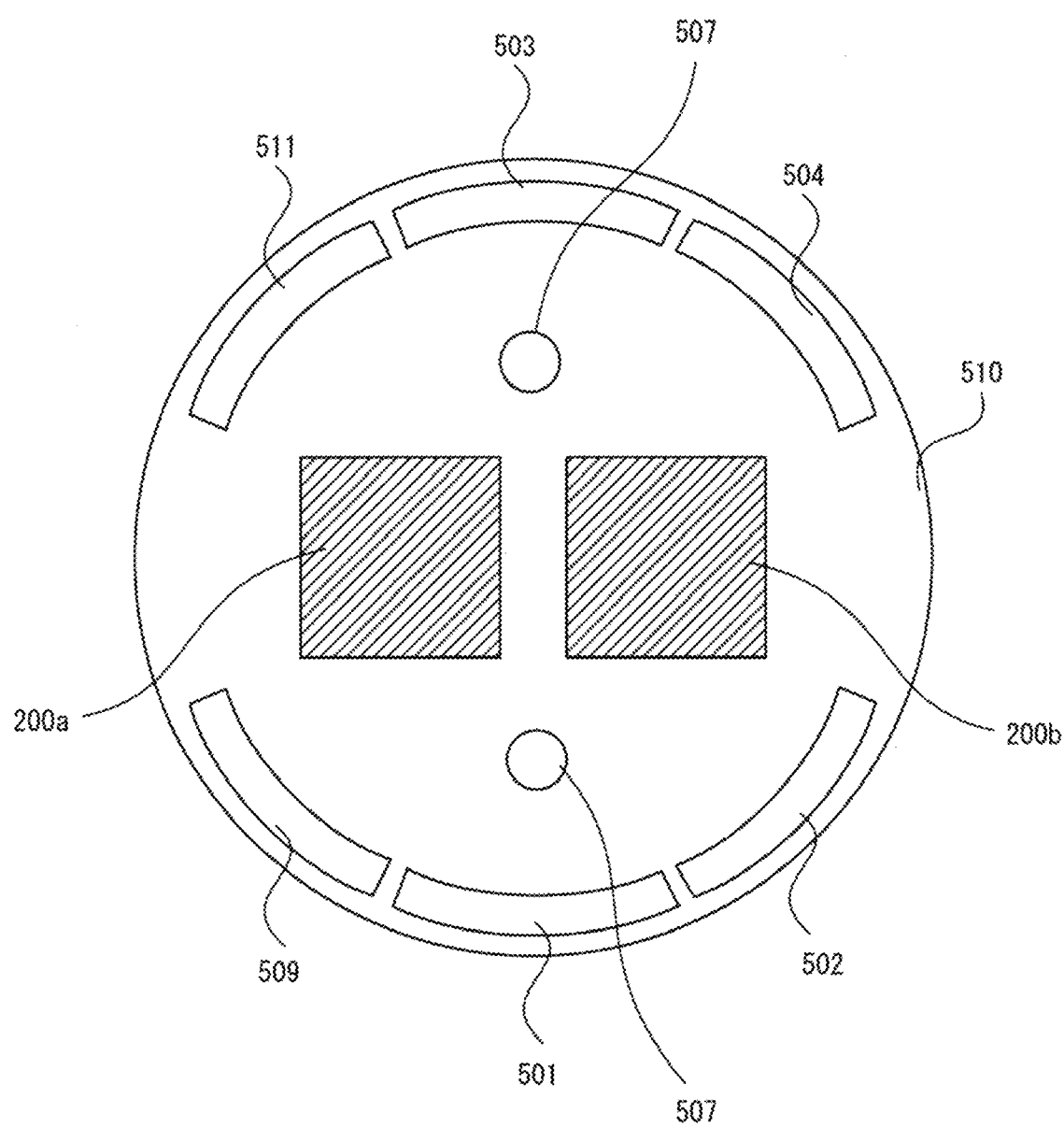
FIG. 17 shows an example of a structure that may be adopted for the objective unit in the third embodiment.

FIG. 17 illustrates the positional arrangement with which radiation ports 501 through 504, 507, 509 and 511, the image-capturing surface 200*a* and the image-capturing surface 200*b* are disposed at the objective unit 510, which faces opposite the target object 5 in the polarization property image measurement device 30 in the embodiment.

Light beams in the various polarization conditions, having undergone intensity modulation at different frequencies F1 through F7, are radiated through the seven radiation ports 501 through 504, 507, 509 and 511 at the polarization property image measurement device 30 in the embodiment. Light beams in the 0° polarization condition, the 45° polarization condition, the 90° polarization condition and the rightward circular polarization condition, having undergone the intensity modulation at the frequencies F1, F2, F3 and F4 different from one another, are radiated through the four radiation ports 501 through 504, as in the polarization property image measurement device 10 in the first embodiment. Through the radiation port 509, a light beam in the 135° polarization condition having undergone intensity modulation at the frequency F5 is radiated. From the radiation port 511, a light beam in the leftward circular polarization condition having undergone intensity modulation at the frequency F6 is radiated. Through the radiation ports 507, unpolarized white light having undergone intensity modulation at the frequency F7 is radiated.

At the image-capturing surfaces 200*a* and 200*b*, disposed at a central area of the objective unit 510, the polarization detection pixels 201 through 204, 209 and 210, the R pixels 205, the G pixels 206 and the B pixels 207 are arrayed by adopting specific patterns such as those shown in FIG. 16.

Figure 18:
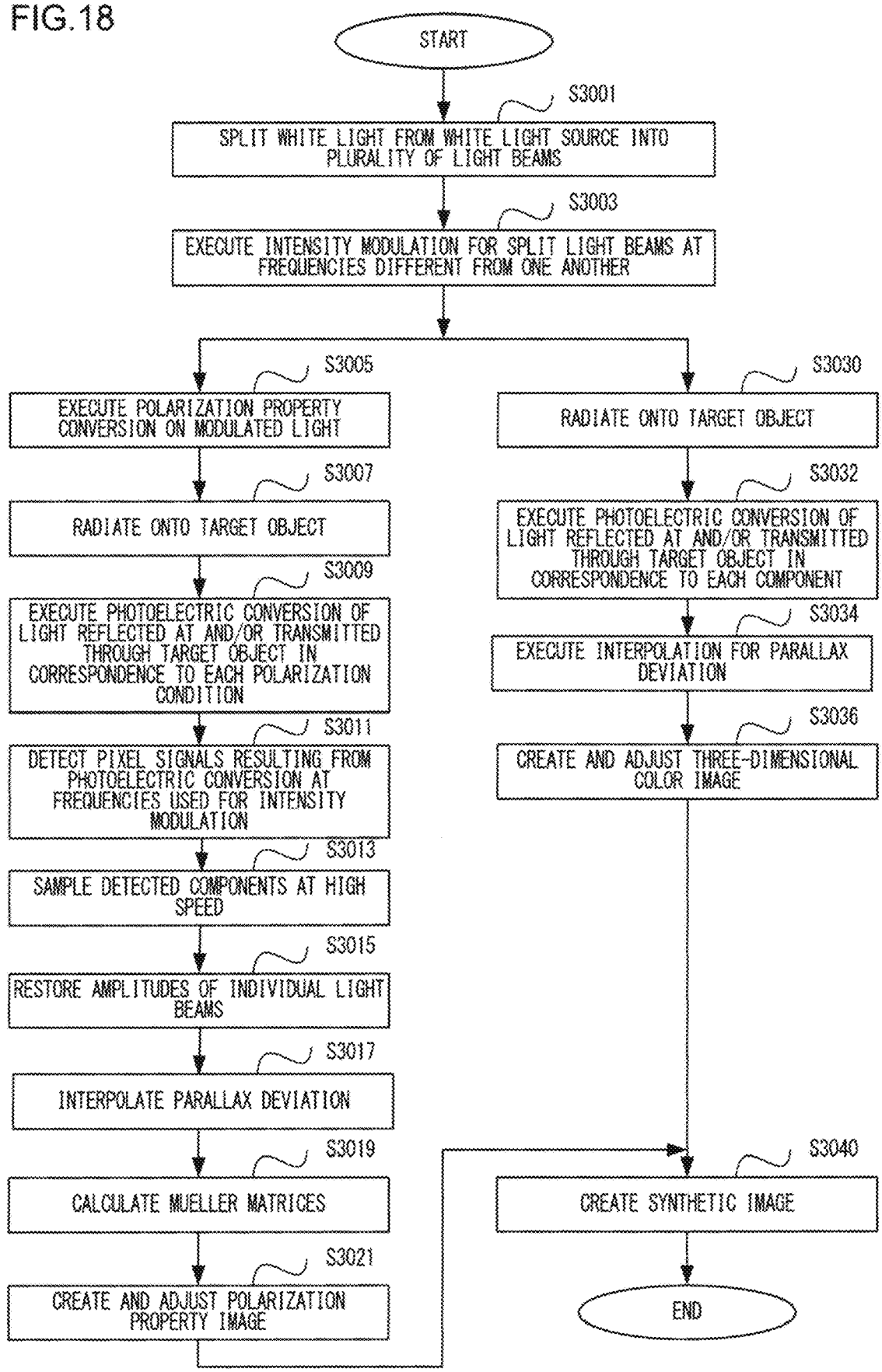
FIG. 18 is a flowchart of the polarization property image creation processing executed in the third embodiment.

FIG. 18 presents a flowchart of a polarization property image measurement method adopted in the polarization property image measurement device 30 in the embodiment. It is distinguishable from the flowchart (see FIG. 10) pertaining to the polarization property image measurement method adopted in the polarization property image measurement device 10 in the first embodiment in that it includes additional steps S3017 and S3034, in which interpolation for the parallax deviation is executed and in that a three-dimensional image is created. Since the processing pertaining to polarization property image creation executed in steps S3001 through S3013 (corresponds to steps S1001 through S1013 in FIG. 10) and the processing pertaining to color image creation executed in step S3030 and step S3032 (corresponds to steps S1030 and S1032 in FIG. 10) are identical to those executed in the first embodiment, except in that the processing is executed in conjunction with the image sensor 100 with a dual structure, i.e., in conjunction with an image sensor 100*a* and an image sensor 100*b* respectively corresponding to the image-capturing surface 200*a* and the image-capturing surface 200*b*, a repeated explanation is not provided.

In step S3015, the parallax deviation interpolation unit 90 restores the amplitudes of light beams in the various polarization conditions, which are needed for purposes of Mueller matrix calculation, in correspondence to both the image sensor 100*a* and the image sensor 100*b*, based upon the polarization property signals output from the discriminating unit 13. The amplitudes can be restored at the respective image sensors 100. Once the amplitudes are restored, the operation proceeds to step S3017.

In step S3017, the parallax deviation interpolation unit 90 calculates the deviation attributable to the parallax effect based upon information indicating the amplitudes having been restored for the light beams in the various polarization conditions and determines corresponding pixel unit blocks on the image-capturing surface 200*a* and the image-capturing surface 200*b* that correspond to each position at the target object 5. In addition, the parallax deviation interpolation unit 90 executes interpolation for sets of information output from pixels corresponding to different polarization conditions in the two corresponding pixel unit blocks at the image-capturing surface 200*a* and the image-capturing surface 200*b*. Once the interpolation of the pixel information is completed, the operation proceeds to step S3019.

In step S3019, the Mueller matrix operation processing unit 21 calculates a Mueller matrix in correspondence to each position at the target object based upon the interpolated pixel information provided by the parallax deviation interpolation unit 90. Once the Mueller matrices have been calculated, the operation proceeds to step S3021. In step S3021, the display adjustment unit 23 creates and adjusts a polarization property image based upon the Mueller matrices having been obtained. Once the polarization property image is created and adjusted, the operation proceeds to step S3040.

For purposes of three-dimensional color image creation, the parallax deviation interpolation unit 90 appends the parallax deviation information having been obtained through step S3017 to the color pixel information and outputs the coupled information to the color image creation processing unit 41 in step S3034. In step S3036, the color image creation processing unit 41 creates a three-dimensional color image based upon the pixel information appended with the parallax information and the color image display adjustment unit 42 adjusts the color image so as to render it ready to be combined with the polarization property image. Once the three-dimensional color image has been adjusted, the operation proceeds to step S3040.

In step S3040, the image synthesis processing unit 43 combines the polarization property image and the three-dimensional color image having been obtained and thus, a synthetic three-dimensional image is created. Once the synthetic image has been obtained, the processing ends.

In addition to the advantages and operations achieved through the first embodiment, the following advantages and operations are realized in the third embodiment described above.

(1) At the polarization property image measurement device 30 achieved in the embodiment, which creates a polarization property image and/or a synthetic image based upon the parallax deviation between the corresponding polarization property pixels disposed at the image-capturing surface 200*a* and the image-capturing surface 200*b*, light beams, originating from the same position at the target object 5 to undergo photoelectric conversion in at least some of the corresponding polarization property pixels 201 through 204, 209 and 210 assume polarization conditions different from each other at the image-capturing surface 200*a* and the image-capturing surface 200*b*. As a result, information pertaining to the depth of the target object 5 can be obtained based upon the parallactic disparity between the two image-capturing surfaces and, at the same time, more accurate Mueller matrices can be measured by using information on light beams in more diverse polarization conditions obtained through direct measurement.

(2) The polarization property image measurement device 30 achieved in the embodiment generates, based upon the parallax deviation, a two-dimensional polarization property image through interpolation of different polarization conditions assumed in light beams received at the corresponding polarization detection pixels 201 through 204, 209 and 210 at the image-capturing surface 200*a* and the image-capturing surface 200*b*, and also creates a synthetic three-dimensional image by mapping the two-dimensional polarization property image on a three-dimensional image created based upon the parallax deviation. As a result, a more stereoscopic polarization property image of the target object 5 can be displayed in a more user-friendly manner.

The following variation is also within the scope of the present invention, and the variation may be adopted in combination with the embodiment described above.

(Variation 1)

The parallax deviation interpolation unit 90 of the polarization property image measurement device 30 achieved in the embodiment described above extracts the amplitudes of the individual light components from signals obtained by differentiating the signals output from the polarization property pixels 201 through 204, 209 and 210 and calculates the deviation attributable to the parallax effect, between the pixel information obtained from the image-capturing surface 200*a* and the pixel information obtained from the image-capturing surface 200*b*. As an alternative, the parallax deviation interpolation unit 90 may analyse the pixel signals output from the color pixels and calculate the deviation attributable to the parallax effect, between the pixel information obtained from the image-capturing surface 200*a* and the pixel information obtained from the image-capturing surface 200*b*. In addition, the parallax deviation interpolation unit 90 may determine deviation attributable to the parallax effect based upon color images created on a temporary basis by using the individual sets of pixel information. In such a case, a polarization property that can be viewed with better ease may be provided in the form of a three-dimensional color image created based upon the parallax deviation between corresponding color pixels.

Fourth Embodiment

A polarization property image measurement device 40 achieved in the fourth embodiment, adopting a structure similar to that of the polarization property image measurement device 10 in the first embodiment, is distinguishable in that near-infrared light is radiated from the light source radiating unit 11 and in that a video clip is generated based upon signals output from pixels that selectively receive near-infrared light (hereafter referred to as IR pixels) disposed at the image-capturing surface 200. Components identical to those in the first embodiment are assigned with the same reference signs as those in the first embodiment so as to preclude the necessity for a repeated explanation thereof wherever possible.

Figure 19:
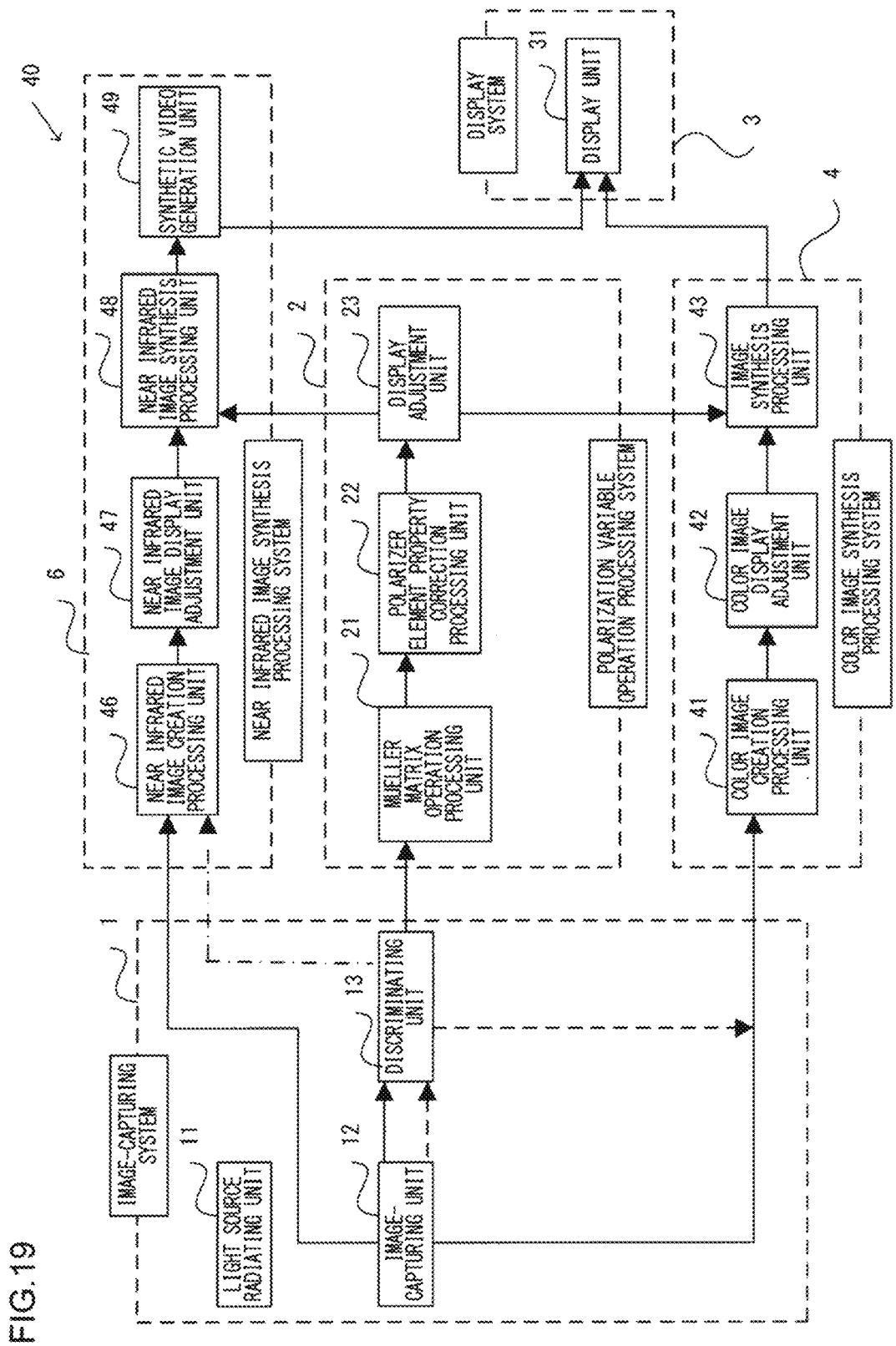
FIG. 19 is a schematic block diagram pertaining to a polarization property image measurement device achieved in a fourth embodiment.

FIG. 19 is a diagram showing the functional blocks in the polarization property image measurement device 40 achieved in the fourth embodiment. The functional blocks in the polarization property image measurement device 40 are configured substantially identically to the functional blocks in the polarization property image measurement device 10 in the first embodiment (see FIG. 1), except that the polarization property image measurement device 40 includes a near-infrared image synthesis processing system 6. The near-infrared image synthesis processing system 6 comprises a near-infrared image creation processing unit 46, a near-infrared image display adjustment unit 47, a near-infrared image synthesis processing unit 48 and a synthetic video generation unit 49.

The light source unit 51 in the light source radiating unit 11 further includes a near-infrared light source such as a near-infrared LED. Near-infrared light output from the near-infrared light source travels through a light path similar to those of the light beams in the various polarization conditions and is radiated from the radiation system objective unit 57.

It is to be noted that the light emitted from the near infrared light source may be split into a plurality of light beams at the light separation unit 52 or undergo intensity modulation at the intensity modulation unit 53 as needed. The wavelength range thereof may be adjusted via the optical property conversion unit 54, as needed. Alternatively, an adjustment may be made as needed so as to, for instance, directly radiate near-infrared light from the light source onto the target object 5. A configuration may be employed in which the near-infrared light that has undergone the intensity modulation undergoes photoelectric conversion and signals resulting from the photoelectric conversion are demodulated at the discriminating unit 13 (see the one-point chain line arrow).

The near-infrared image synthesis processing system 6 creates an image of the target object 5 formed with near infrared light radiated onto the target object 5 (hereafter referred to as a near infrared image) based upon pixel signals output from the IR pixels and creates a synthetic video clip by combining the near-infrared image with a polarization property image output from the polarization variable operation processing system 2. The near-infrared image creation processing unit 46 creates the near infrared image through image processing of the known art based upon the pixel signals output from the IR pixels disposed at the image-capturing unit 12. The near infrared image thus created is adjusted at the near infrared image display adjustment unit 47 so as to render it ready to be combined with the polarization property image. The near infrared image display adjustment unit 47 may adjust the near infrared image so as to enhance structural elements or the like of the target object 5, the characteristics of which cannot be visually verified with visible light readily but can be verified with infrared light. The adjusted near infrared image is then provided to the near infrared image synthesis processing system 48.

The near infrared image synthesis processing unit 48 combines the polarization property image provided from the display adjustment unit 23 with the near infrared image provided from the near infrared image display adjustment unit 47 and thus creates a synthetic near infrared image, i.e., a composite image created by combining the polarization property image and the near infrared image. The near infrared image synthesis processing unit 48 provides the synthetic near infrared image thus created to the synthetic video generation unit 49.

It is to be noted that the near infrared image synthesis processing unit 48 may output the near infrared image having been created to the display unit 31 to be brought up on display at the display unit 31 as needed.

The synthetic video generation unit 49 creates a synthetic video clip by setting a predetermined number of synthetic images having been obtained in a sequence matching the order with which the individual images have been captured. A synthetic video clip may be created by obtaining images at a frame rate equal to or higher than 1 Hz and setting the images thus obtained in time sequence. It is desirable that the frame rate at which such a synthetic video clip is generated be at least 10 Hz, and it is even more desirable to generate the synthetic video clip at a frame rate equal to or higher than 30 Hz. The synthetic video clip thus generated is provided to the display unit 31, where it is brought up on display.

It is to be noted that the infrared light to be radiated onto the target object may also undergo intensity modulation and detection processing for pixel signal separation. Under such circumstances, it is not strictly necessary to execute the detection processing for the light beams in the various polarization conditions and the detection processing for the near infrared light in synchronization with each other, as long as a video clip can be generated at a desired frame rate, which allows only a slight time lag, shorter than the time intervals between the individual frames.

Figure 20:
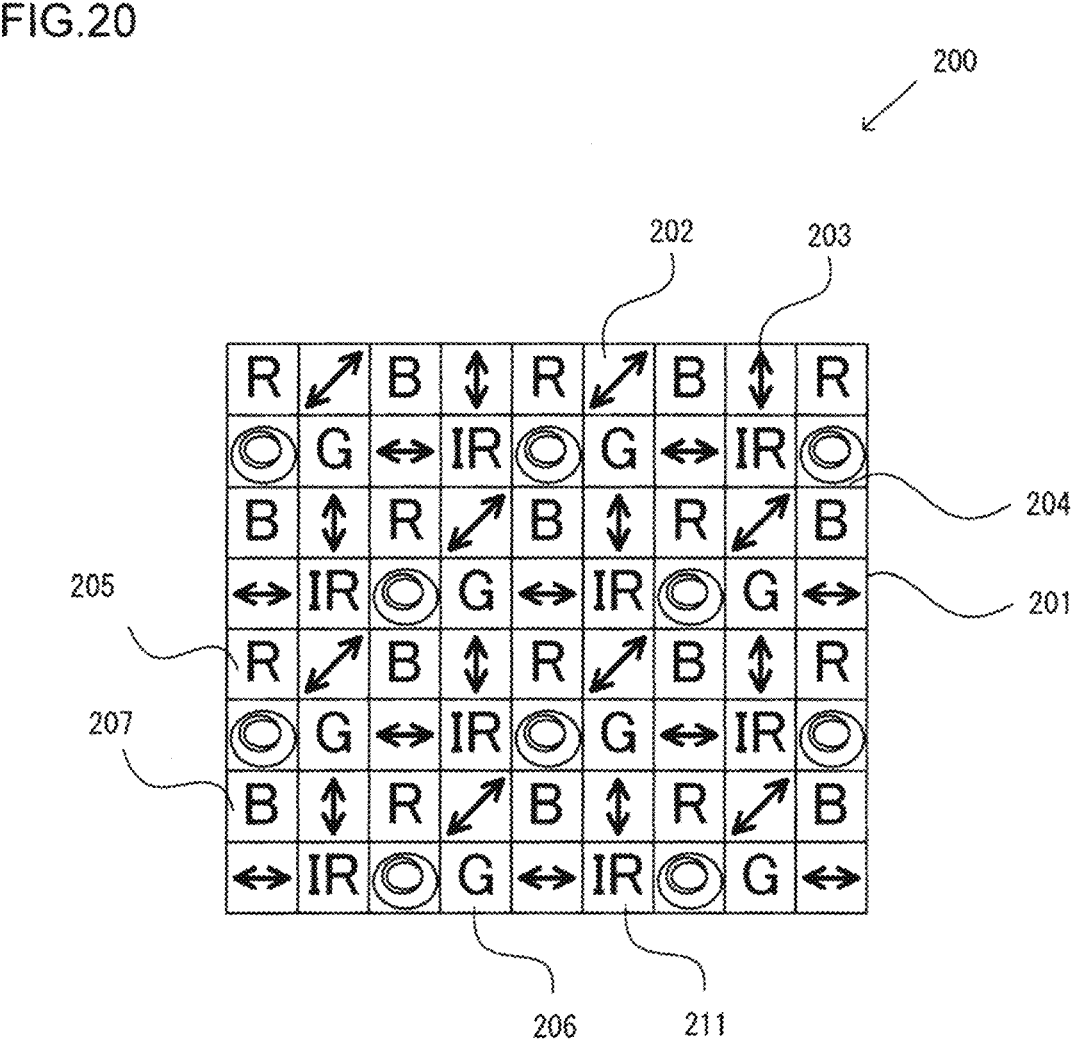
FIG. 20 shows an example of a pixel array that may be adopted at the image-capturing surface in the fourth embodiment.

FIG. 20 schematically illustrates part of the pixel array at the image-capturing surface 200 of the image sensor 100 in the polarization property image measurement device 40 achieved in the fourth embodiment. At the image-capturing surface 200, 0° pixels 201, 45° pixels 202, 90° pixels 203, rightward circular polarization pixels 204, R pixels 205, G pixels 206, B pixels 207 and IR pixels 211 are disposed.

Figure 21:
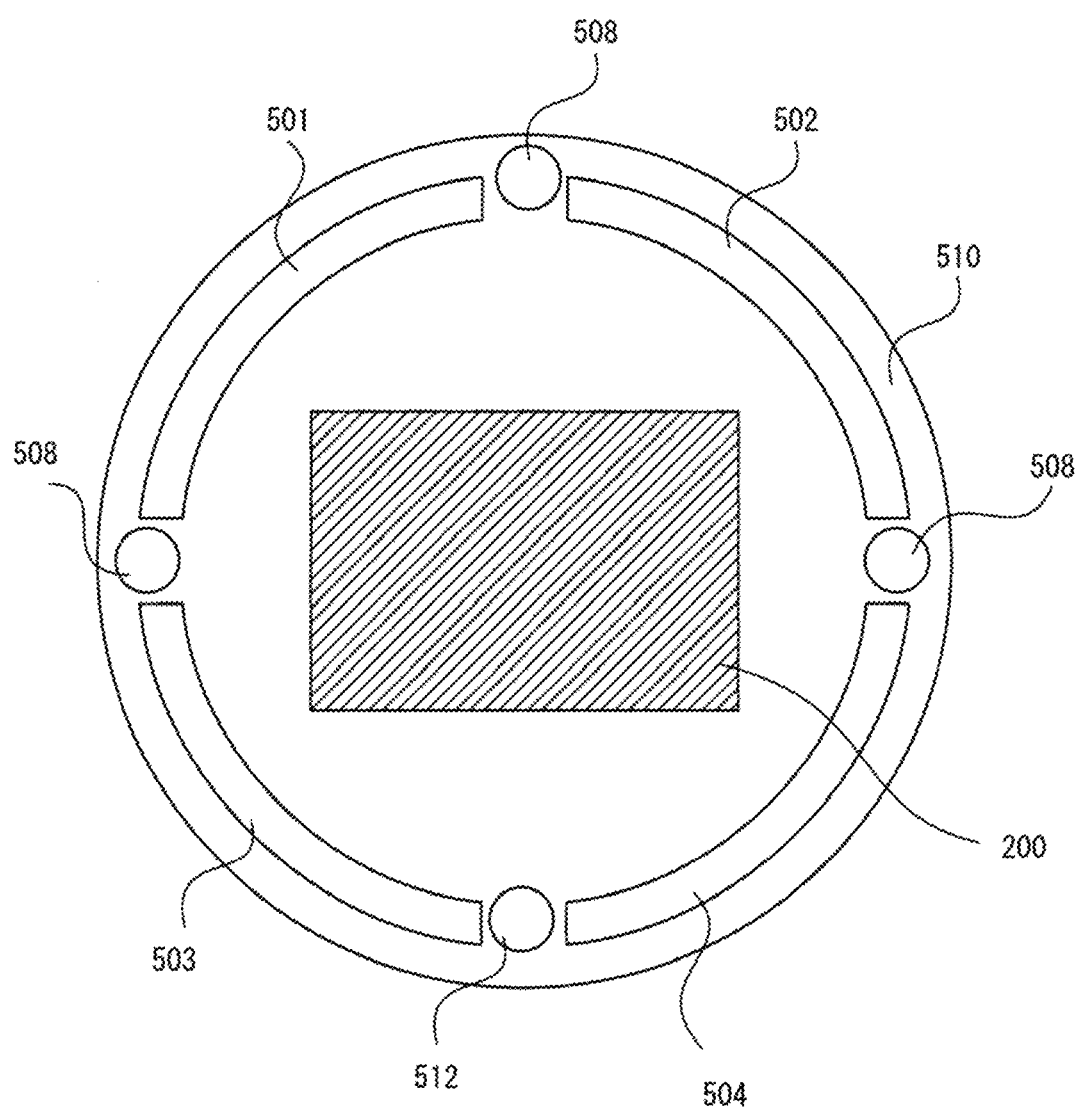
FIG. 21 shows an example of a structure that may be adopted for the objective unit in the fourth embodiment.

FIG. 21 illustrates the positional arrangement with which the image-capturing surface 200 and the radiation ports 501 through 504, 508 and 512 are disposed at the objective unit 510, which faces opposite the target object 5 in the polarization property image measurement device 40 in the embodiment.

Light beams in the various polarization conditions, having undergone intensity modulation at different frequencies F1, F2, F3 and F4, are radiated through the four radiation ports 501 through 504 at the polarization property image measurement device 40 in the embodiment, as in the polarization property image measurement device 10 in the first embodiment. White light, having undergone intensity modulation at a frequency F5 different from the frequencies F1, F2, F3 and F4, is radiated through white light radiation ports 508. From a near infrared light radiation port 512, near infrared light is radiated. It is to be noted that the present invention may be adopted in conjunction with radiation ports for white light and near infrared light disposed in a positional arrangement and in quantities other than those in the figure.

At the image-capturing surface 200, disposed at a central area of the objective unit 510, the polarization detection pixels 201 through 204, the R pixels 205, the G pixels 206, the B pixels 207 and the IR pixels 211 are arrayed by adopting a specific pattern such as that shown in FIG. 20.

Figure 22:
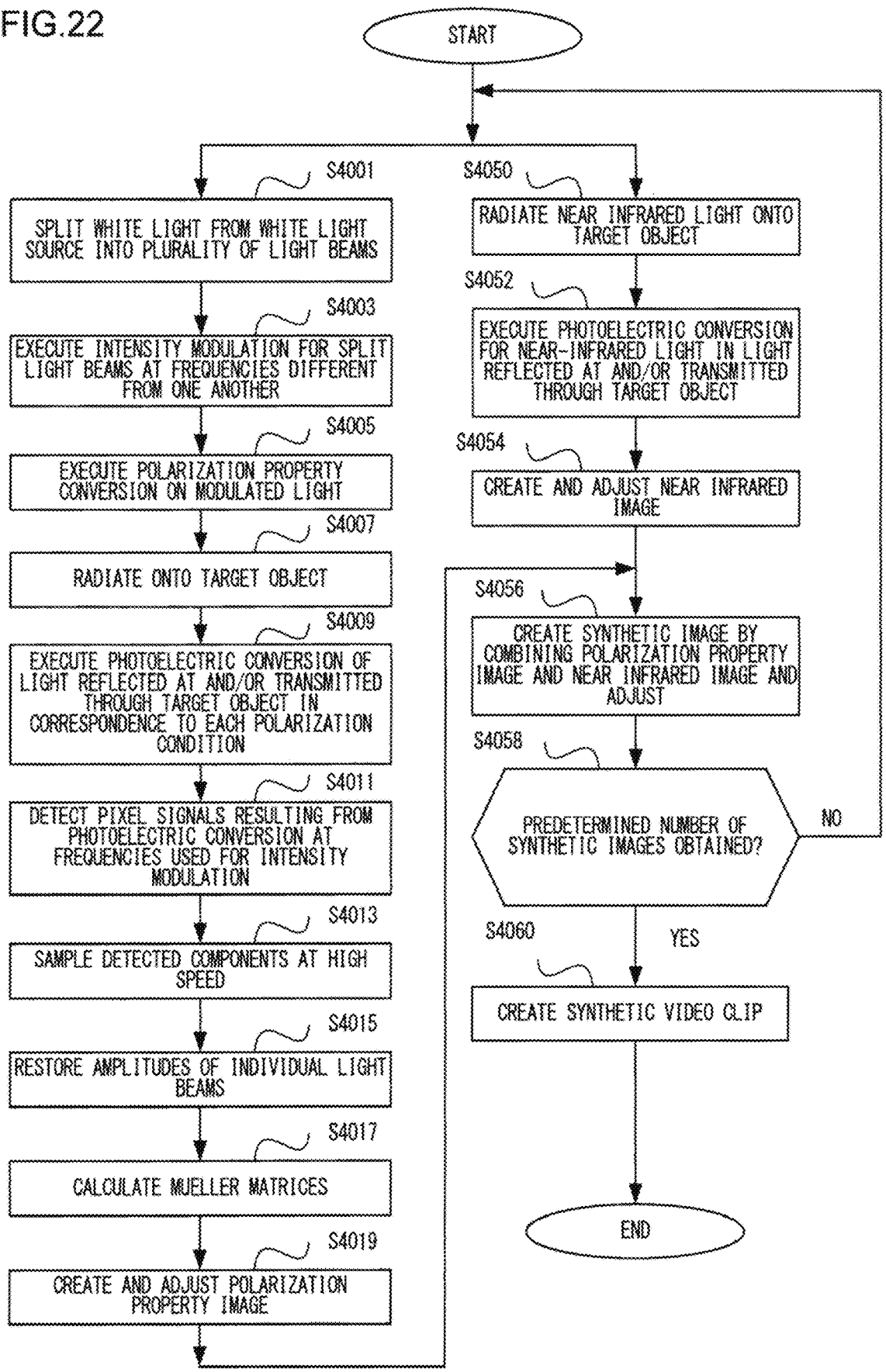
FIG. 22 is a flowchart of the polarization property image creation processing executed in the fourth embodiment.

FIG. 22 presents a flowchart of synthetic video generation executed in the polarization property image measurement device 40 in the embodiment. The processing pertaining to polarization property image creation, executed in step S4001 through step S4019 (correspond to steps S1001 through S1019 in FIG. 10) is identical to that executed in the first embodiment, and a repeated explanation is not provided.

In step S4050, the light source radiating unit 11 radiates infrared light onto the target object 5. Once the target object has been irradiated, the operation proceeds to step S4052. In step S4052, near infrared light in the light scattered at the target object 5, undergoes photoelectric conversion at the IR pixels 211 in the image sensor 100. Once the photoelectric conversion has been completed, the operation proceeds to step S4054. In step S4054, the near infrared image creation processing unit 46 creates a near infrared image and the near infrared image display adjustment unit 47 adjusts the near infrared image to render it ready to be combined with the polarization property image. Once the near infrared image has been adjusted, the operation proceeds to step S4056.

In step S4056, the near infrared image synthesis processing unit 48 creates a synthetic image by combining the polarization property image and the near infrared image, and provides the synthetic image thus created to the synthetic video generation unit 49. Once the synthetic image is provided to the synthetic video generation unit 49, the operation proceeds to step S4058. In step S4058, the synthetic video generation unit 49 makes a decision as to whether or not a predetermined number of synthetic images have been obtained. If the number of synthetic images having been obtained is equal to or greater than a predetermined value, the synthetic video generation unit 49 makes an affirmative decision in step S4058 and the operation proceeds to step S4060. If, on the other hand, the number of synthetic images having been obtained is smaller the predetermined value, the synthetic video generation unit 49 makes a negative decision in step S4058, and the operation returns to step S4001 and step S4050. In step S4060, the synthetic video generation unit 49 creates a synthetic video clip with the predetermined number of synthetic images having been obtained. Once the synthetic video clip has been created, the processing ends.

In addition to the advantages and operations achieved through the first embodiment, the following advantage and operation are realized through the fourth embodiment described above.

(1) The polarization property image measurement device 40 achieved in the embodiment radiates near infrared light onto the target object 5 and creates a synthetic image by combining a near infrared image and a polarization property image and a synthetic video clip based upon signals resulting from photoelectric conversion of near infrared light scattered at the target object 5. Thus, imaging of the target object 5 is enabled by using near infrared light assuring a high level of biological tissue permeability, and at the same time, the polarization characteristics of the target object 5 can be displayed.

The following variations are also within the scope of the present invention, and any of the variations may be adopted in combination with the embodiment described above.

(Variation 1)

In the embodiment described above, the radiation ports 501 through 504, through which light beams in the various polarization conditions are radiated, are each disposed at one location at the objective unit 510 in the polarization property image measurement device 40. As an alternative, the radiation ports 501 through 504 for light beams in the various polarization conditions may each be disposed at a plurality of positions on the objective unit 510, and the light beams in the various polarization conditions may each be split and radiated through the individual radiation ports 501 through 504. Through these measures, specular reflection of intense light radiated from a single radiation port can be prevented and ultimately, saturation of pixel signals can be prevented.

Figure 23:
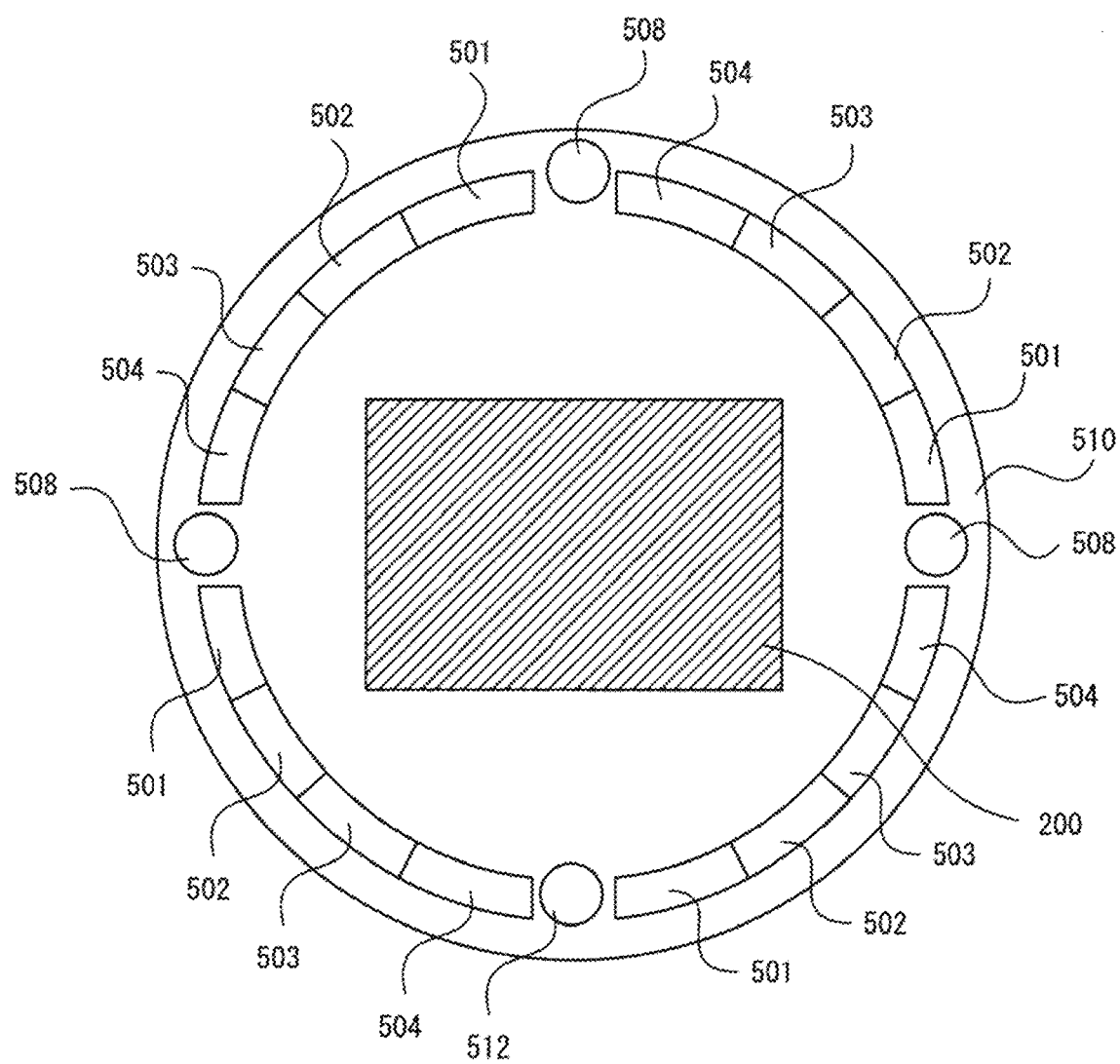
FIG. 23 shows an example of a structure that may be adopted for the objective unit in an embodiment.

FIG. 23 illustrates the structure of an objective unit 510 having radiation ports 501 through 504, each disposed at four locations in correspondence to light in a given polarization condition. It is preferable that the radiation ports 501 through 504 for light beams in the various polarization conditions be set symmetrically around the center of the objective unit 510, at positions optimally dispersed on the objective unit 510.

(Variation 2)

The polarization property image measurement device 40 achieved in variation 1 of the embodiment adopts a structure in which light in each polarization condition is split and the split light beams are then radiated through a plurality of corresponding radiation ports among the radiation ports 501 through 504 so as to prevent specular reflection. As an alternative, the polarization property image measurement device 40 may adopt a structure that includes an exposure time setting unit that adjusts and sets exposure time by comparing the intensity of a pixel signal output from a target pixel with the intensity levels of the pixel signals output from some of, or all of the other pixels disposed at the image-capturing surface 200. This structure makes it possible to prevent saturation of pixel signals even when there is pronounced specular reflection. Such an exposure time setting unit should be disposed at an optimal position in the processing circuit laminated at the image sensor 100 for each pixel and should set the optimal exposure time based upon the difference between the intensity of the pixel signal output from the target pixel and a value representing the average intensity among the pixel signals output from pixels present in the surrounding area over a predetermined range.

It is to be noted that the exposure time setting unit may adjust the exposure time based upon the largest value or the smallest value among the intensity levels of the pixel signals output from a plurality of pixels at the image-capturing surface or based upon the dynamic range or the like pertaining to the intensity levels of the pixel signals output from the plurality of pixels.

Figure 24:
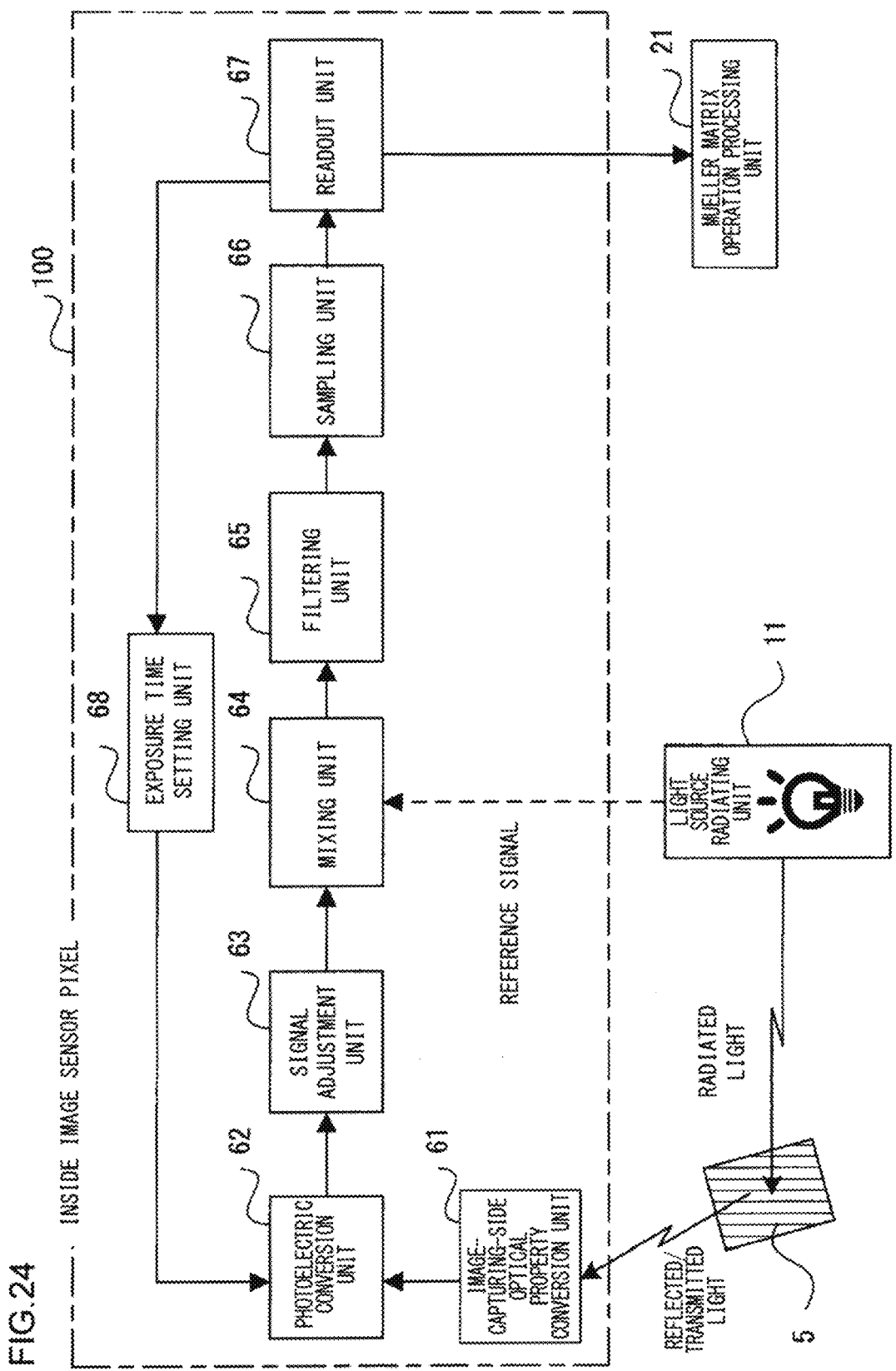
FIG. 24 is a schematic diagram showing functional blocks disposed in a pixel in an embodiment.

FIG. 24 is a schematic diagram showing an exposure time setting unit 68 included as part of the internal structure of a pixel at the image sensor. The exposure time setting unit 68 obtains data indicating the intensity of the pixel signal from the readout unit 67 and sets an exposure time for the photoelectric conversion to be executed at the photoelectric conversion unit 62. As a result, the exposure time can be adjusted quickly through internal processing executed at the image sensor 100.

It is to be noted that the exposure time setting unit 68 may be disposed outside the target pixel, instead.

(Variation 3)

The R pixels 205, the G pixels 206, the B pixels 207 and the IR pixels 211 in the polarization property image measurement device 40 in the embodiment do not need the circuits and the laminated layer portions engaged in the processing for differentiating the components having undergone intensity modulation in correspondence to the various frequencies, such as the signal adjustment unit 63, the mixing unit 64, the filtering unit 65, the sampling unit 66 and the readout unit 67 included in each polarization detection pixel. Accordingly, the circuit and the laminated layer portions engaged in the processing for the signal adjustment unit 63, the mixing unit 64, the filtering unit 65, the sampling unit 66 and the readout unit 67 of a polarization detection pixel among the polarization detection pixels 201 through 204 may be laminated in the vacant lamination area at an adjacent pixel among the R pixels 205, the G pixels 206, the B pixels 207 and the IR pixels 211. Through these measures, the processing circuits can be integrated with a better rate and the polarization condition can be differentiated efficiently via the processing circuits laminated at adjacent color pixels.

Figure 25:
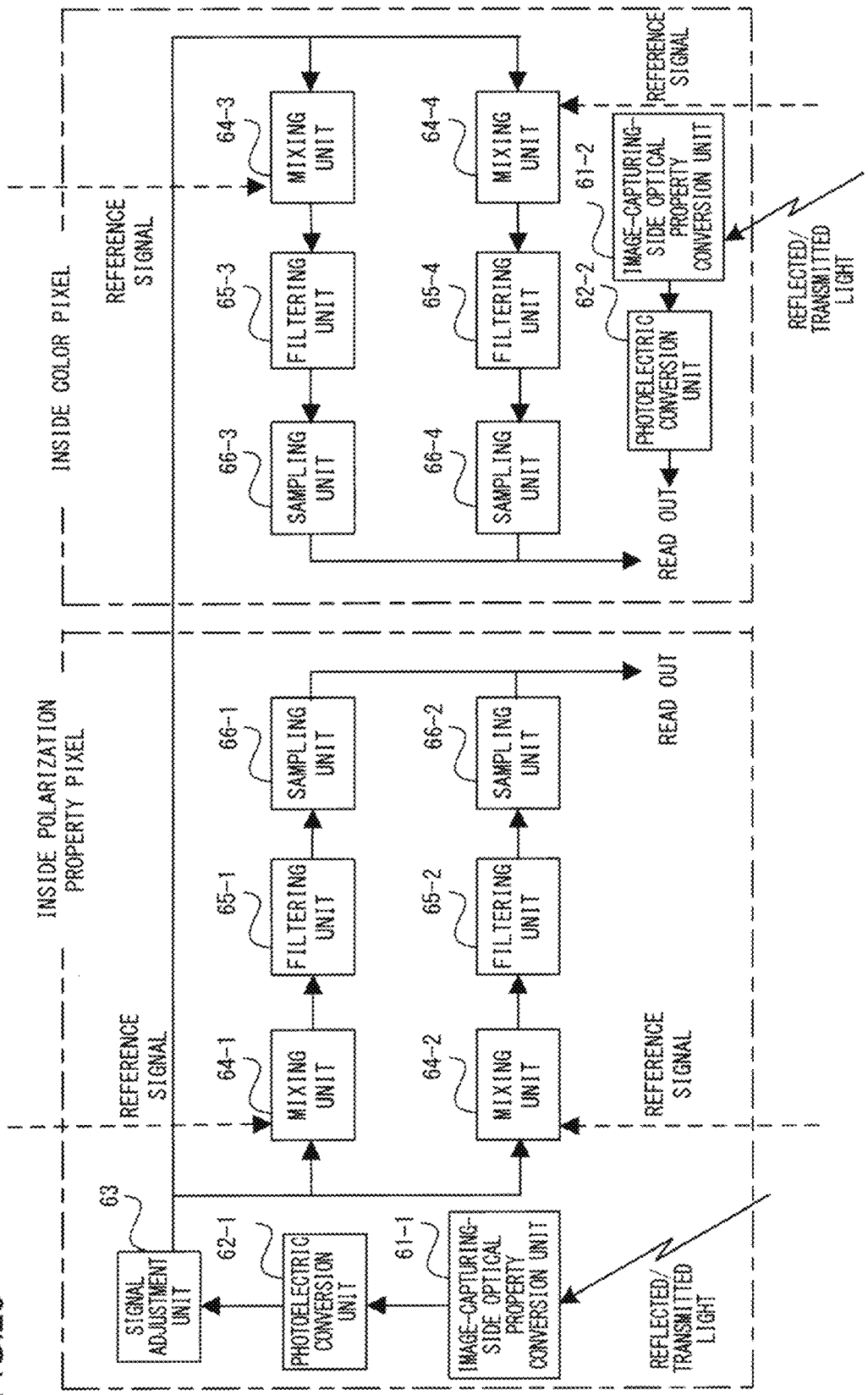
FIG. 25 is a diagram illustrating how functional blocks may be disposed in a plurality of pixels in an embodiment.

FIG. 25 presents an example of an arrangement that may be adopted in conjunction with the various functional blocks when differentiation processing is executed to differentiate polarization conditions via processing circuits laminated at color pixels. While the pixel signal output from a given polarization property pixel undergoes differentiation processing by using four different frequencies, each corresponding to one of the four different types of radiated light beams, differentiation processing in correspondence to two of the four frequencies is executed at a color pixel adjacent to the given polarization property pixel in this example.

Light in the color corresponding to the particular color pixel, included in the light having been scattered at the target object 5 and having entered the color pixel, is selectively transmitted through an image-capturing-side optical property conversion unit 61-2, and then undergoes photoelectric conversion at a photoelectric conversion unit 62-2 in the color pixel. The signal resulting from the photoelectric conversion then undergoes readout processing.

Light assuming a specific polarization condition included in the light having been scattered at the target object 5 and having entered the polarization property pixel, is selectively transmitted through an image-capturing-side optical property conversion unit 61-1 and then undergoes photoelectric conversion at a photoelectric conversion unit 62-1 in the polarization property pixel. The pixel signal resulting from the photoelectric conversion is input to the signal adjustment unit 63. The signal adjustment unit 63 adjusts the pixel signal to render it ready for frequency separation through, for instance, current/voltage conversion, splits the output into four separate signals, outputs two of the four signals to mixing units 64-1 and 64-2 within the polarization property pixel and outputs the remaining two signals to mixing units 64-3 and 64-4 disposed in the processing circuit within the adjacent color pixel. The signals input to the various mixing units 64-1, 64-2, 64-3 and 64-4 undergo multiplication processing or the like executed by using reference signals at corresponding frequencies, and then undergo filtering processing and sampling processing at corresponding filtering units 65-1, 65-2, 65-3 and 65-4 and corresponding sampling units 66-1, 66-2, 66-3 and 66-4 respectively, before they are read out.

It is to be noted that while differentiation processing is executed within the polarization property pixel in correspondence to two types of radiated light beams among the four different types of radiated light beams in the description provided above, adjustment may be made so as to assign a given session of differentiation processing corresponding to a given type of radiated light beam to the processing circuit in an optimal pixel. For instance, one session of differentiation processing may be executed within the polarization property pixel, two sessions of differentiation processing may be executed in the adjacent R pixel and the remaining session of differentiation processing may be executed in the G pixel disposed adjacent to the polarization property pixel. In addition, differentiation processing for a polarization property pixel may be designated to be executed in the processing circuit of an adjacent IR pixel as well.

(Variation 4)

While the light emitted from the light source 51 is first split into separate light beams which then undergo intensity modulation in the light source radiating unit 11 of the polarization property image measurement device 40 achieved in the embodiment, an alternative structure in which light having undergone intensity modulation is directly emitted from an LED may be adopted.

Figure 26:
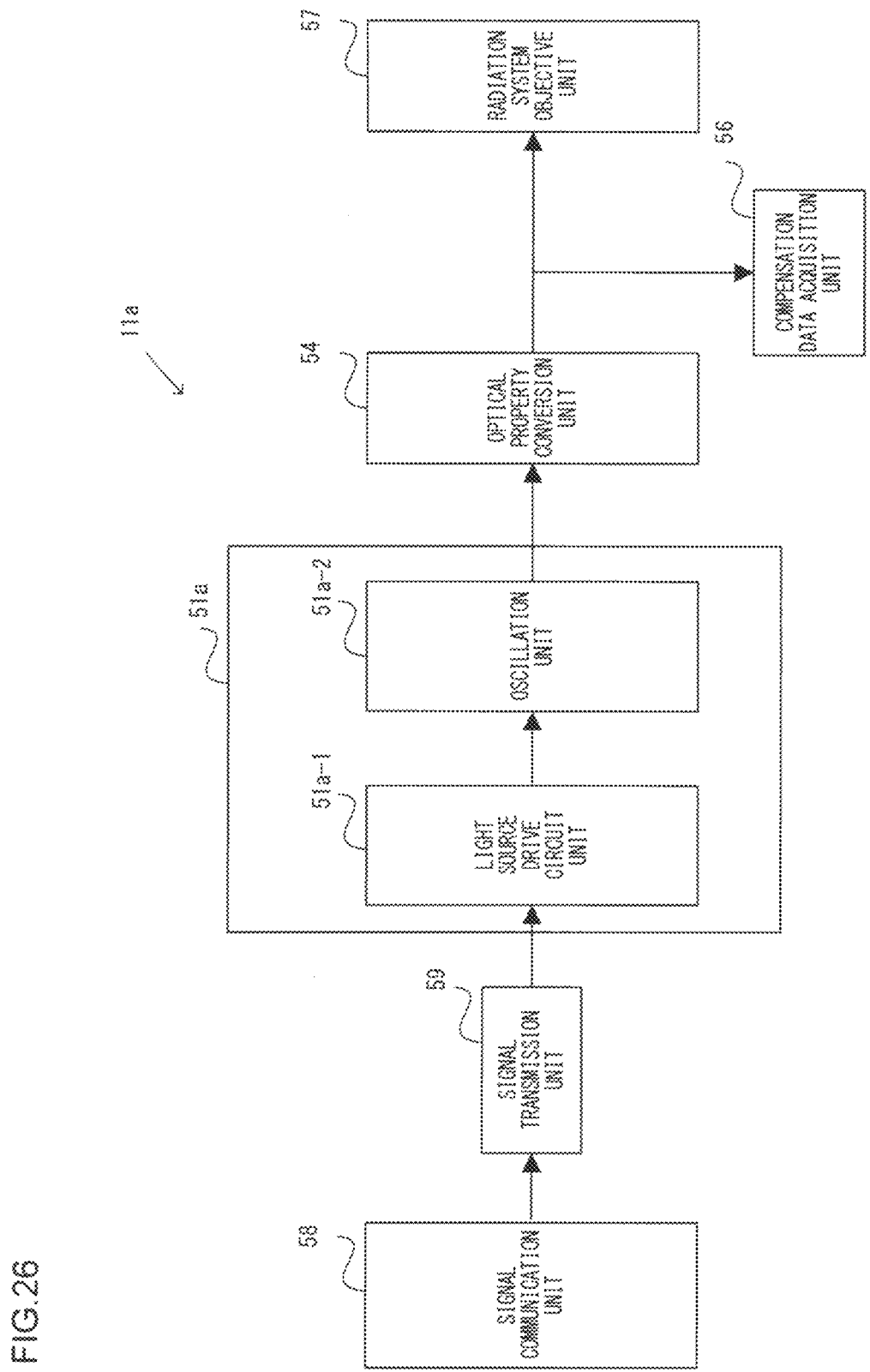
FIG. 26 is a schematic block diagram pertaining to a light source radiating unit achieved in an embodiment.

FIG. 26 shows functional blocks of a light source radiating unit 11a that includes a light source configured with an LED that emits light having undergone intensity modulation. The light source radiating unit 11a includes a signal communication unit 58, a signal transmission unit 59, a light source unit 51a, an optical property conversion unit 54, a compensation data acquisition unit 56 and a radiation system objective unit 57. In addition, the light source unit 51a includes a light source drive circuit unit 51a-1 and an oscillation unit 51a-2. Since the optical property conversion unit 54, the compensation data acquisition unit 56 and the radiation system objective unit 57 are identical to those in the embodiments described earlier, a repeated explanation is not provided.

The signal communication unit 58, constituted with, for instance, a function generator, generates an AC voltage signal that assumes a predetermined frequency and a predetermined waveform. The signal communication unit 58 outputs the AC voltage signal having been generated to the signal transmission unit 59. The signal transmission unit 59, constituted with an electrical cable or the like through which the voltage signal is transmitted, provides the AC voltage signal generated at the signal communication unit 58 to the light source drive circuit unit 51a-1. When controlling the radiating unit from a remote location, as in an endoscope, the live tissue can be observed in a less invasive manner via the signal transmission unit 59, constituted with a narrow tube or the like, disposed between the processing device at which the signal communication unit 58 is disposed and the light source unit 51a.

It is to be noted that the signal transmission unit 59 may be disposed between the light source drive circuit unit 51a-1 and the oscillation unit 51a-2.

The light source drive circuit unit 51a-1, which is equivalent to, for instance, an LED chip or the like, adjusts a current to be used to oscillate radiation light based upon the voltage signal provided through the signal transmission unit 59. The current signal having been adjusted is then output to the oscillation unit 51a-2. The oscillation unit 51a-2, which includes a light emitting element constituted of an LED, emits the light having undergone intensity modulation at a predetermined frequency, based upon the current signal input thereto from the light source drive circuit unit 51a-1.

The polarization property image measurement device 40 that includes the light source radiating unit 11a described above is capable of radiating light emitted from the LED, which has low coherence or no coherence, while assuming a simpler structure. In this polarization property image measurement device, frequency separation processing can be executed without allowing interference by light at a frequency assuming a value equal to the sum of, or the difference between different modulation frequencies and thus, the likelihood of noise occurring at the time of demodulation can be lowered.

Fifth Embodiment

While a polarization property image measurement device 20 achieved in the fifth embodiment adopts a structure similar to that of the polarization property image measurement device 10 in the first embodiment, it is distinguishable in that it includes a phase modulation unit 53'disposed between the intensity modulation unit 53 and the optical property conversion unit 54. Components identical to those in the first embodiment are assigned with the same reference signs as those in the first embodiment so as to preclude the necessity for a repeated explanation thereof wherever possible.

The intensity modulation unit 53 in the embodiment executes intensity modulation for a plurality of light beams at a single frequency. The phase modulation unit 53' sets different intensity modulation phases from one light beam to another among the plurality of light beams. The intensity modulation phases may be varied from one light beam to another either through phase labelling, whereby fixed values representing different intensity modulation phases are each set for one of the plurality of light beams or through frequency labelling, whereby a different frequency is selected when cyclically changing the intensity modulation phase. In more specific terms, phase labelling is achieved by taking different fixed values for (I), representing the intensity modulation phase, the number of which matches the number of light beams, in equation (6) below expressing the intensity of light having undergone intensity modulation. Frequency labelling is achieved by cyclically changing the intensity modulation phase (I) with a cosine wave and varying the angular speed w corresponding to the frequency so that the angular speed w takes different values, the number of which corresponds to the number of light beams.

$$I(t) \mapsto \tfrac{1}{2}I(t)[1+\cos(\Omega t+\phi)] = \tfrac{1}{2}E_0^2[1+\cos(\Omega t+\phi)], \phi = m\cos(wt) \quad (6)$$

It is to be noted that I represents the light intensity, E represents the electric field vector of the light, and $\Omega$ represents the angular speed corresponding to the frequency at which intensity modulation is executed at the intensity modulation unit 53. The plurality of light beams having undergone the intensity modulation then undergo polarization condition conversion at the optical property conversion unit 54. The plurality of light beams, having undergone the polarization condition conversion are simultaneously radiated from the light source radiating unit 11.

Light having undergone the intensity modulation can be differentiated to determine its origin, i.e., the light beam in a specific polarization condition initially radiated from the light source radiating unit 11, as in the first embodiment, via the discriminating unit 13 that detects the light at the phase set for the light for purposes of the intensity modulation. For instance, the discriminating unit 13 may use phase information pertaining to a given light beam having been labelled through phase labelling so as to differentiate the received light to determine its origin, i.e., the light having been radiated at a specific phase, through multiplication processing executed by using a sine wave and a cosine wave corresponding to the particular phase. As an alternative, the discriminating unit 13 may separate light beams one from another in correspondence to the frequencies of the light resulting from frequency labelling so as to differentiate the received light to determine its origin, i.e., the light having been radiated at a specific phase.

While various embodiments and variations thereof have been described above, the present invention is in no way limited to the particulars of these embodiments and variations. Any other mode conceivable within the scope of the technical teaching of the present invention is also within the scope of the present invention.

What is claimed is:

1. An image sensor, comprising:
a light receiver that is disposed in a first substrate and receives light from a target object onto which a plurality of light beams having different polarization conditions are radiated, the light receiver comprising a plurality of first photoelectric converters photoelectrically converting respective light beams having different polarization conditions from one another; and
a differentiator that is disposed in a second substrate deposited on the first substrate and to differentiate, among signals output from the plurality of the first photoelectrically converters, each signal from other signals so as to determine an origin of the signal as one of the plurality of light beams.

2. The image sensor according to claim 1, further comprising:
a first radiator that radiates the plurality of light beams onto the target object after subjecting the plurality of light beams to intensity modulation at frequencies different from one another, wherein:
the plurality of first photoelectric converters photoelectrically convert light from the target object in correspondence to each of different polarization conditions; and
the differentiator detects signals at the different frequencies from individual signals output from each of the plurality of first photoelectric converters corresponding to respective different polarization conditions and differentiates each signal from other signals so as to determine the origin of the signal as one of the plurality of light beams.

3. The image sensor according to claim 2, further comprising:
a memory chip that is deposited in the image sensor and configured to store signals output from the plurality of first photoelectric converter.

4. The image sensor according to claim 3, wherein:
a through via is disposed at at least one of the first substrate, the second substrate and the memory chip so as to connect a circuit disposed at a front surface and a circuit disposed at a back surface.

5. The image sensor according to claim 1, wherein:
the light receiver comprises a plurality of pixel blocks comprising the plurality of first photoelectric converters that photoelectrically convert respective light beams having different polarization conditions from one another; and
each of the plurality of pixel blocks output a polarization property signal of the target object.

6. The image sensor according to claim 2, wherein:
the first radiator simultaneously radiates the plurality of light beams in different polarization conditions; and
the differentiator concurrently detects the signals individually output from the plurality of first photoelectric converters.

7. The image sensor according to claim 1, wherein:
the light receiver comprises a plurality of second photoelectric converters that photoelectrically convert visible light from the target object; and
the image sensor further comprises visible image creator that creates an image of the target object based upon signals individually output from the plurality of second photoelectric converters.

8. The image sensor according to claim 7, further comprising:
a second radiator that radiates white light onto the target object, wherein:
the light receivers further comprises color filters each disposed on a light entry side of one of the second photoelectric converters; and
the visible image creator creates a color image of the target object based upon the signals individually output from the plurality of second photoelectric converters.

9. The image sensor according to claim 1, wherein:
the light receivers further comprises a plurality of third photoelectric converters that photoelectrically convert near infrared light from the target object; and
the image sensor further comprises near-infrared imager creator that creates an image of the target object based upon signals individually output from the plurality of third photoelectric converters.

10. The image sensor according to claim 1, further comprising:
a polarization property display image creator that creates a polarization property display image indicating physical properties of the target object based upon the signals having been differentiated from one another by the differentiator.

11. The image sensor according to claim 10, further comprising:
a polarization property video creator that creates a video clip containing a plurality of polarization property display images.

12. The image sensor according to claim 2, wherein:
the light receivers comprises a first pixel block and a second pixel block that receive light from the target object, at angles of incidence different from each other; and
the image sensor comprises a unitpolarization property display image creator that creates a polarization property display image based upon a parallax deviation between the first photoelectric converters in the first pixel block and the first photoelectric converters in the second pixel block, that correspond to each other.

13. The image sensor according to claim 8, wherein:
the light receiver comprises a first color pixel block and a second color pixel block that receive light from the target object onto which light from the second radiator is radiated, at angles of incidence different from each other; and
the visible image creator creates a three-dimensional color image based upon a parallax deviation between the second photoelectric converters in the first color pixel block and the second photoelectric converters in the second color pixel block, that correspond to each other.

14. The image sensor according to claim 1, wherein:
the light receiver comprises a processing circuit disposed in correspondence to each pixel at the light receiver so as to process a signal output from the pixel, and the processing circuit is disposed in a substrate deposited on the first substrate in correspondence to each of the plurality of first photoelectric converters.

15. A measurement device comprising the image sensor according to claim 1.

16. The measurement device according to claim 15, further comprising:
a processor that calculates a Mueller matrix based upon a signal output from the differentiator.

17. A measurement method, comprising:
- photoelectrically converting light from a target object onto which a plurality of light beams having different polarization conditions are radiated, by a light receiver that is disposed in a first substrate of an image sensor and comprises a plurality of first photoelectric converters photoelectrically converting respective light beams having different polarization conditions from one another; and
- differentiating, among signals output from the plurality of the first photoelectrically converters, each signal from other signals so as to determine an origin of the signal as one of the plurality of light beams by a differentiator that is disposed in a second substrate deposited on the first substrate in the image sensor.

18. The measurement method according to claim 17, further comprising:
- calculating a Mueller matrix based upon a signal output from the differentiator.

19. The image sensor according to claim 1, further comprising:
- a first radiator that radiates the plurality of light beams in different polarization conditions onto the target object after subjecting the plurality of light beams to intensity modulation at phases different from one another, wherein:
- the plurality of first photoelectric converters photoelectrically convert light from the target object onto which the plurality of light beams are radiated from the first radiator in correspondence to each of the different polarization conditions; and
- the differentiator detects signals at the different phases from individual signals output from each of the plurality of first photoelectric converters corresponding to respective different polarization conditions and differentiates each signal from other signals so as to determine the origin of the signal as one of the plurality of light beams.

* * * * *

UNITED STATES PATENT AND TRADEMARK OFFICE
CERTIFICATE OF CORRECTION

PATENT NO. : 11,268,900 B2
APPLICATION NO. : 16/781474
DATED : March 8, 2022
INVENTOR(S) : Takanori Kojima et al.

It is certified that error appears in the above-identified patent and that said Letters Patent is hereby corrected as shown below:

In the Claims

Column 37, Line 64:
In Claim 7, delete "comprises" and insert --comprises a--.

Column 38, Line 12:
In Claim 9, delete "receivers" and insert --receiver--.

Column 38, Line 38:
In Claim 12, delete "unitpolarization" and insert --polarization--.

Signed and Sealed this
Twenty-first Day of June, 2022

Katherine Kelly Vidal
*Director of the United States Patent and Trademark Office*